(12) United States Patent
Gerlach et al.

(10) Patent No.: US 7,909,858 B2
(45) Date of Patent: Mar. 22, 2011

(54) BONE PLATE SYSTEMS USING PROVISIONAL FIXATION

(75) Inventors: Darin Gerlach, Cordova, TN (US); Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 744 days.

(21) Appl. No.: 11/644,303

(22) Filed: Dec. 22, 2006

(65) Prior Publication Data

US 2007/0276386 A1    Nov. 29, 2007

Related U.S. Application Data

(63) Continuation of application No. 10/952,047, filed on Sep. 28, 2004, now abandoned, which is a continuation-in-part of application No. 10/673,833, filed on Sep. 29, 2003, now Pat. No. 7,179,260.

(51) Int. Cl.
*A61B 17/80* (2006.01)

(52) U.S. Cl. .......................................... 606/280; 606/281

(58) Field of Classification Search ................... 606/280, 606/291, 281, 286, 324, 915, 289, 282, 329, 606/70

See application file for complete search history.

(56) References Cited

U.S. PATENT DOCUMENTS

| | | |
|---|---|---|
| 575,631 A | 1/1897 | Brooks |
| 902,040 A | 10/1908 | Wyckoff |
| 2,501,978 A | 3/1950 | Wichman |
| 2,699,774 A | 1/1955 | Livingston |
| 3,530,854 A | 9/1970 | Kearney |
| 3,866,607 A | 2/1975 | Forsythe et al. |
| RE28,841 E | 6/1976 | Allgower et al. |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,565,193 A | 1/1986 | Streli |
| 4,622,959 A | 11/1986 | Marcus |
| 4,657,001 A | 4/1987 | Fixel |
| 4,836,196 A | 6/1989 | Park et al. |
| 4,838,252 A | 6/1989 | Klaue |
| 4,927,421 A | 5/1990 | Goble et al. |
| 4,988,350 A | 1/1991 | Herzberg |
| 5,002,544 A | 3/1991 | Klaue et al. |

(Continued)

FOREIGN PATENT DOCUMENTS

DE    43 43 117 A1    6/1995

(Continued)

OTHER PUBLICATIONS

Brochure entitled Introducing Peak™ Polyaxial Anterior Cervical Plate, by Depuy Motech, one page, undated.

(Continued)

*Primary Examiner* — Pedro Philogene
(74) *Attorney, Agent, or Firm* — Fish & Richardson P.C.

(57) ABSTRACT

Bone plates with an upper surface, a bone contacting surface, and a plurality of holes extending through the upper and bone contact surfaces for receiving bone screws are disclosed. Each hole interchangeably accepts a compression screw for compression of a fracture and a locking screw that threads into the bone plate. Provisional fixation of a bone plate to a bone may be accomplished using provisional fixation pins through the screw-receiving holes of the bone plate.

10 Claims, 17 Drawing Sheets

U.S. PATENT DOCUMENTS

| | | | |
|---|---|---|---|
| 5,013,313 A | 5/1991 | Surer | |
| 5,041,113 A | 8/1991 | Biedermann et al. | |
| 5,041,114 A | 8/1991 | Chapman et al. | |
| 5,041,116 A | 8/1991 | Wilson | |
| 5,053,036 A | 10/1991 | Perren et al. | |
| 5,057,111 A | 10/1991 | Park | |
| 5,085,660 A | 2/1992 | Lin | |
| 5,127,914 A | 7/1992 | Calderale et al. | |
| 5,129,901 A | 7/1992 | Decoste | |
| 5,151,103 A | 9/1992 | Tepic et al. | |
| 5,190,544 A | 3/1993 | Chapman et al. | |
| 5,197,966 A | 3/1993 | Sommerkamp | |
| 5,261,910 A | 11/1993 | Warden et al. | |
| 5,269,784 A | 12/1993 | Mast | |
| 5,275,601 A | 1/1994 | Gogolewski et al. | |
| 5,304,180 A | 4/1994 | Slocum | |
| 5,312,410 A | 5/1994 | Miller et al. | |
| 5,324,290 A | 6/1994 | Zdeblick et al. | |
| 5,324,291 A | 6/1994 | Ries et al. | |
| 5,364,398 A | 11/1994 | Chapman et al. | |
| 5,387,217 A | 2/1995 | Sefcik et al. | |
| 5,395,374 A | 3/1995 | Miller et al. | |
| 5,415,658 A | 5/1995 | Kilpela et al. | |
| 5,423,820 A | 6/1995 | Miller et al. | |
| 5,429,641 A | 7/1995 | Gotfried | |
| 5,431,659 A | 7/1995 | Rose, Jr. et al. | |
| 5,470,333 A | 11/1995 | Ray | |
| 5,474,553 A | 12/1995 | Baumgart | |
| 5,486,176 A | 1/1996 | Hildebrand et al. | |
| 5,501,684 A | 3/1996 | Schlapfer et al. | |
| 5,520,690 A | 5/1996 | Errico et al. | |
| 5,527,310 A | 6/1996 | Cole et al. | |
| 5,536,127 A | 7/1996 | Pennig | |
| 5,549,612 A | 8/1996 | Yapp et al. | |
| 5,569,253 A | 10/1996 | Farris et al. | |
| 5,571,184 A | 11/1996 | DeSatnick | |
| 5,601,553 A | 2/1997 | Trebing et al. | |
| 5,607,428 A | 3/1997 | Lin | |
| 5,609,596 A | 3/1997 | Pepper | |
| 5,616,144 A | 4/1997 | Yapp et al. | |
| 5,665,088 A | 9/1997 | Gil et al. | |
| 5,676,666 A | 10/1997 | Oxland et al. | |
| 5,676,667 A * | 10/1997 | Hausman | 606/281 |
| 5,681,311 A | 10/1997 | Foley et al. | |
| 5,681,312 A | 10/1997 | Yuan et al. | |
| 5,702,399 A | 12/1997 | Kilpela et al. | |
| 5,709,686 A * | 1/1998 | Talos et al. | 606/281 |
| 5,713,900 A | 2/1998 | Benzel et al. | |
| 5,713,902 A | 2/1998 | Friedl | |
| 5,735,853 A | 4/1998 | Olerud | |
| 5,741,256 A | 4/1998 | Bresina | |
| 5,741,258 A | 4/1998 | Klaue et al. | |
| 5,742,872 A | 4/1998 | Copperwheat et al. | |
| 5,772,662 A | 6/1998 | Chapman et al. | |
| 5,776,194 A | 7/1998 | Mikol et al. | |
| 5,788,697 A | 8/1998 | Kilpela et al. | |
| 5,797,911 A | 8/1998 | Sherman et al. | |
| 5,797,912 A | 8/1998 | Runciman et al. | |
| 5,800,433 A | 9/1998 | Benzel et al. | |
| 5,807,396 A | 9/1998 | Raveh | |
| 5,810,823 A | 9/1998 | Klaue et al. | |
| 5,836,950 A | 11/1998 | Hansson | |
| 5,843,082 A | 12/1998 | Yuan et al. | |
| 5,891,145 A | 4/1999 | Morrison et al. | |
| 5,893,856 A | 4/1999 | Jacob et al. | |
| 5,902,305 A | 5/1999 | Beger et al. | |
| 5,904,683 A | 5/1999 | Pohndorf et al. | |
| 5,935,130 A | 8/1999 | Kipela et al. | |
| 5,935,133 A | 8/1999 | Wagner et al. | |
| 5,935,169 A | 8/1999 | Chan | |
| 5,954,722 A | 9/1999 | Bono | |
| 5,957,953 A | 9/1999 | DiPoto et al. | |
| 5,961,521 A | 10/1999 | Roger | |
| 5,964,767 A | 10/1999 | Tapia | |
| 5,964,769 A | 10/1999 | Wagner et al. | |
| 5,968,046 A | 10/1999 | Castleman | |
| 5,976,141 A | 11/1999 | Haag et al. | |
| 5,997,541 A | 12/1999 | Schenk | |
| 6,001,130 A | 12/1999 | Bryan et al. | |
| 6,017,345 A | 1/2000 | Richelsoph | |
| 6,022,350 A | 2/2000 | Ganem | |
| 6,022,352 A | 2/2000 | Vandewalle | |
| 6,030,389 A | 2/2000 | Wagner et al. | |
| 6,053,921 A | 4/2000 | Wagner et al. | |
| 6,096,040 A | 8/2000 | Esser | |
| 6,129,730 A | 10/2000 | Bono et al. | |
| 6,139,552 A | 10/2000 | Horiuchi | |
| 6,166,861 A | 12/2000 | Koizumi | |
| 6,176,861 B1 | 1/2001 | Bernstein et al. | |
| 6,193,721 B1 | 2/2001 | Michelson | |
| 6,206,881 B1 * | 3/2001 | Frigg et al. | 606/291 |
| 6,221,074 B1 | 4/2001 | Cole et al. | |
| 6,235,031 B1 | 5/2001 | Hodgeman et al. | |
| 6,235,033 B1 | 5/2001 | Brace et al. | |
| 6,306,136 B1 | 10/2001 | Baccelli | |
| 6,306,140 B1 | 10/2001 | Siddiqui | |
| 6,322,562 B1 | 11/2001 | Wolter | |
| 6,336,930 B1 | 1/2002 | Stalcup et al. | |
| 6,355,043 B1 | 3/2002 | Adam | |
| 6,358,250 B1 | 3/2002 | Orbay | |
| 6,361,537 B1 | 3/2002 | Anderson | |
| 6,364,882 B1 * | 4/2002 | Orbay | 606/86 B |
| 6,364,885 B1 | 4/2002 | Kilpela et al. | |
| 6,391,030 B1 | 5/2002 | Wagner et al. | |
| 6,406,477 B1 | 6/2002 | Fujiwara | |
| 6,413,259 B1 | 7/2002 | Lyons et al. | |
| 6,423,066 B1 | 7/2002 | Harder et al. | |
| 6,428,542 B1 | 8/2002 | Michelson | |
| 6,440,135 B2 | 8/2002 | Orbay et al. | |
| 6,443,954 B1 | 9/2002 | Bramlet et al. | |
| 6,454,769 B2 | 9/2002 | Wagner et al. | |
| 6,475,218 B2 | 11/2002 | Gournay et al. | |
| 6,506,191 B1 | 1/2003 | Joos | |
| 6,520,965 B2 | 2/2003 | Chervitz et al. | |
| 6,595,994 B2 | 7/2003 | Kilpela et al. | |
| 6,623,486 B1 | 9/2003 | Weaver et al. | |
| 6,648,889 B2 | 11/2003 | Bramlet et al. | |
| 6,652,529 B2 | 11/2003 | Swanson | |
| 6,656,179 B1 | 12/2003 | Schaefer et al. | |
| 6,682,533 B1 | 1/2004 | Diinsdale et al. | |
| 6,730,091 B1 | 5/2004 | Pfefferle et al. | |
| 6,821,278 B2 | 11/2004 | Frigg et al. | |
| 6,960,213 B2 | 11/2005 | Chervitz et al. | |
| 7,052,499 B2 | 5/2006 | Steger et al. | |
| 7,137,987 B2 * | 11/2006 | Patterson et al. | 606/291 |
| 7,179,260 B2 | 2/2007 | Gerlach et al. | |
| 7,282,053 B2 | 10/2007 | Orbay | |
| 7,306,600 B2 | 12/2007 | Roth et al. | |
| 7,316,687 B2 | 1/2008 | Aikins et al. | |
| 7,341,589 B2 | 3/2008 | Weaver et al. | |
| 7,344,537 B1 | 3/2008 | Mueller | |
| 7,537,596 B2 * | 5/2009 | Jensen | 606/280 |
| 7,695,472 B2 * | 4/2010 | Young | 606/70 |
| 2001/0011172 A1 | 8/2001 | Orbay et al. | |
| 2001/0037112 A1 | 11/2001 | Brace et al. | |
| 2001/0047174 A1 | 11/2001 | Donno et al. | |
| 2002/0013587 A1 | 1/2002 | Winquist et al. | |
| 2002/0045896 A1 | 4/2002 | Michelson | |
| 2002/0045901 A1 | 4/2002 | Wagner et al. | |
| 2002/0049445 A1 | 4/2002 | Hall, IV et al. | |
| 2002/0058940 A1 | 5/2002 | Frigg et al. | |
| 2002/0058943 A1 | 5/2002 | Kilpela et al. | |
| 2002/0072753 A1 | 6/2002 | Cohen | |
| 2002/0143333 A1 | 10/2002 | von Hoffmann et al. | |
| 2002/0143338 A1 | 10/2002 | Orbay et al. | |
| 2002/0156473 A1 | 10/2002 | Branket et al. | |
| 2002/0156475 A1 | 10/2002 | Lerch et al. | |
| 2002/0161370 A1 | 10/2002 | Frigg et al. | |
| 2002/0183752 A1 | 12/2002 | Steiner et al. | |
| 2002/0183754 A1 | 12/2002 | Michelson | |
| 2002/0183755 A1 | 12/2002 | Michelson | |
| 2003/0018335 A1 | 1/2003 | Michelson | |
| 2003/0040749 A1 | 2/2003 | Grabowski et al. | |
| 2003/0040752 A1 | 2/2003 | Kitchens | |
| 2003/0060827 A1 | 3/2003 | Coughln | |
| 2003/0074000 A1 | 4/2003 | Roth et al. | |
| 2003/0078581 A1 | 4/2003 | Frei et al. | |

| | | | |
|---|---|---|---|
| 2003/0187440 | A1 | 10/2003 | Richelsoph et al. |
| 2003/0220641 | A1 | 11/2003 | Thelen et al. |
| 2004/0019353 | A1 | 1/2004 | Fried et al. |
| 2004/0030342 | A1 | 2/2004 | Trieu et al. |
| 2004/0044345 | A1 | 3/2004 | DeMoss et al. |
| 2004/0059334 | A1 | 3/2004 | Weaver et al. |
| 2004/0073218 | A1 | 4/2004 | Dahners |
| 2004/0087954 | A1 | 5/2004 | Allen et al. |
| 2004/0097942 | A1 | 5/2004 | Allen |
| 2004/0102773 | A1 | 5/2004 | Morrison et al. |
| 2004/0138666 | A1 | 7/2004 | Molz, IV et al. |
| 2004/0199169 | A1 | 10/2004 | Koons et al. |
| 2004/0210217 | A1 | 10/2004 | Baynham et al. |
| 2004/0210219 | A1 | 10/2004 | Bray |
| 2004/0220566 | A1 | 11/2004 | Bray |
| 2005/0010223 | A1 | 1/2005 | Gotfried |
| 2005/0049593 | A1 | 3/2005 | Duong et al. |
| 2005/0055024 | A1 | 3/2005 | James et al. |
| 2005/0070904 | A1 | 3/2005 | Gerlach |
| 2005/0107796 | A1 | 5/2005 | Gerlach et al. |
| 2005/0273099 | A1 | 12/2005 | Baccelli et al. |
| 2006/0079900 | A1 | 4/2006 | Mathieu et al. |
| 2006/0116678 | A1 | 6/2006 | Impellizzeri |
| 2006/0149247 | A1 | 7/2006 | Frigg et al. |
| 2006/0149265 | A1 | 7/2006 | James |
| 2006/0167464 | A1 | 7/2006 | Allen et al. |

FOREIGN PATENT DOCUMENTS

| | | |
|---|---|---|
| DE | 196 29 011 A1 | 1/1998 |
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| FR | 2 757 370 | 6/1998 |
| JP | 2002-082896 | 3/2002 |
| WO | 97/09000 | 3/1997 |
| WO | 99/38447 | 8/1999 |
| WO | 00/53110 | 9/2000 |
| WO | 00/53111 | 9/2000 |
| WO | WO 01/19264 A2 | 3/2001 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |
| WO | WO 2005/032386 A1 | 4/2005 |
| WO | WO 2006/007965 A1 | 1/2006 |

OTHER PUBLICATIONS

Brochure entitled Introducing the Profile™ Anterior Thoracolumbar Compression Plate, by Dupuy Motech, one page, undated.
Baumgaertel, et al., "Fracture healing in biological plate osteosynthesis," *Injury*, 29(Supp. 3):S-C3-S-C6 (1998).
Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).
Farouk, er al., "Minimally invasive plate osteosynthesis and vascularity: preliminary results of a cadaver injection study," *Injury*, 28(Supp. 1):S-A7-S-A12 (1997).
Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).
Frigg et al., "The development of the distal femur Less Invasive Stabilization System (LISS)," *Injury, Int. J. Care Injured*, 32(S-C24-31 (2001).
Gerber, et al., "Biological internal fixation of fractures," *Arch. Orthop. Trauma Surg.*, 109:295-303 (1990).
Karnezis, et al., "'Biological' internal fixation of long bone fractures: a biomechanical study of a 'noncontact' plate system," *Injury*, 29(9):689-695 (1998).
Koval, et al., "Distal Femoral Fixation: A Biochemical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).
Krettek, et al., "Intraoperative control of axes, rotation and length in femoral and tibial fractures," *Injury*, 29(Supp. 3):S-C-29-S-C39 (1998).
Marti, et al., "Biomechanical Evaluation of the Less Invasive Stabilization System for the Internal Fixation of Distal Femur Fractures," *Journal of Orthopaedic Trauma*, 15(7):482-487, 2001.
Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).
Mudgal, et al., 'Plate and Screw Design in Fractures of the Hand and Wrist,' *Clinical Orthopaedics and Related Research*, 445:68-80 (2006).
Rüedi, et al., "New Techniques in Indirect Reduction of Long Bone Fractures," *Clinical Orthopaedics and Related Research*, No. 347:27-34 (1998).
Schavan, et al.,"LISS—The Less Invasive Stabilization System for Metaphyseal Fractures of Femur and Tibia," *OTA 98 Posters* (1998).
Basic Percutaneous Instrument Set for 4.5mm LCP Condylar Plates (Synthes Large Fragment LCP System). Guide. Synthes (USA), 2005.
Bolhofner, Brett R. et al. "The Results of Open Reduction and Internal Fixation of Distal Femur Fractures Using a Biologic (Indirect) Reduction Technique." Journal of Orthopaedic Trauma. vol. 10. (No. 6) 1996: 372-377.
Brace et al. U.S. Appl. No. 09/453,911: Bone Fixation Assembly. Second Information Disclosure Statement Under 37 C.F.R. § 1.97 and § 1.98. Oct. 2, 2000.
Brace et al. U.S. Appl. No. 09/848,251: Bone Fixation Assembly. Information Disclosure Statement Under 37 C.F.R. § 1.97 and § 1.98. May 4, 2001.
Fitzpatrick, Daniel C. et al. "Relative Stability of Conventional and Locked Plating Fixation in Osteoporotic Bone." Article Submission to Journal of Bone and Joint Surgery. Apr. 18, 2005.
Haas, N.P., et. al., "LISS—Less Invasive Stabilization System—A New Internal Fixator for Distal Femur Fractures," OP J., vol. 13(3), pp. 340-344, Georg Thieme Verlag, Dec. 1997 (original in German, translation to English attached with certification).
Kassab, Safa S. et al. "Patients Treated for Nonunions with Plate and Screw Fixation and Adjunctive Locking Nuts." Clinical Orthopaedics and Related Research. No. 347. Feb. 1998: 86-92.
Kolodziej, Patricia et al. "Biomechanical Evaluation of the Schuhli Nut." Clinical Orthopaedics and Related Research. No. 347. Feb. 1998: 79-85.
Koval et al. "Distal Femoral Fixation: A Biochemical Comparison of the Standard Condylar Buttress Plate, a Locked Buttress Plate, and the 95-Degree Blade Plate". Journal of Orthopaedic Trauma. vol. 11.(No. 7) (OVID electronic database version) Oct. 1997: 521-524.
Koval et al. "Distal Femoral Fixation: A Biochemical Comparison of the Standard Condylar Buttress Plate, a Locked Buttress Plate, and the 95-Degree Blade Plate". Journal of Orthopaedic Trauma. vol. 11 (No. 7) (in color and as published on Internet) Oct. 1997: 521-524.
St. Arenas et al. "Evolution of the Locked Internal Fixator (PC-Fix: Part II)" Injury: International Journal of the Care of the Injured AO ASIF Scientific Supplement. vol. 32, Supplement 2. Elsevier Science Ltd., Sep. 2001.
Schandelmaier et al. "Less Invasive Stabilization System (LISS) for the Distal Femur." Injury: International Journal of the Care of the Injured. AO ASIF Scientific Supplement. vol. 32, Supplement 3, Dec. 2001.
Less Invasive Stablization System (LISS)—Distal Femur Technique Guide. Synthes (USA), 2000.
Less Invasive Stablization System (LISS) Technique Guide. Synthes (USA), 2000.
Nemecek, Deborah. Faxed Letter to Jeff Mast, M.D. Regarding Schuhli Surgical Technique Guide Updates to Illustrations. Jun. 15, 1998.
Nemecek, Deborah. Faxed Letter to Jeff Mast, M.D. Regarding Schuhli Surgical Technique Guide Approval Request for Illustration Changes and Narrative for New X-Ray Case. Jun. 23, 1998.

Nemecek, Deborah. Faxed Letter to Jeff Mast, M.D. Regarding Schuhli Surgical Technique Guide Requesting Approval of Additional Warning Required by FDA and Change of Case #3. Aug. 7, 1998.

Order Granting/Denying Request for Ex Parte Reexamination for U.S. Appl. No. 90/009,377 dated Feb. 13, 2009.

Order Granting/Denying Request for Ex Parte Reexamination for U.S. Appl. No. 90/009,378 dated Feb. 14, 2009.

Perren, Stephan M. et al. "Early Temporary Porosis of Bone Induced by Internal Fixation Implants: A Reaction to Necrosis, Not to Stress Protection?" Clinical Orthopaedics and Related Research.No. 232. Jul. 1998: 139-151.

Rothenberg, Peter. Paoli Spirit. (Publication for Synthes Consultants) vol. 14, Issue 2. Jun. 1999.

Schuhli: Technique Guide—An Adjunct to Plating Problematic Fractures. Synthes (USA) 1998.

*Synthes (U.S.A.)* v. *Smith & Nephew, Inc.*, 03-0084 (E.D. Pa.). (SEALED) Smith & Nephew's Statement of Undisputed Facts in Support of Its Opposition to Synthes Motion for Summary Judgment of No Invalidity of the Weaver Patents over the K982222 Reference. Sep. 29, 2008.

*Synthes (U.S.A.)* v. *Smith & Nephew, Inc.*, 03-0084 (E.D. Pa.). Declarations of Robert A. King in Support of Smith & Nephew, Inc.'s Motion for Partial Summary Judgment of Invalidity of Claims 10-12 of U.S. Patent No. 6,623,486. Sep. 10, 2008.

*Synthes (U.S.A.)* v. *Smith & Nephew, Inc.*, 03-0084 (E.D. Pa.). Declaration of J. Lawrence Marsh, M.D. in Support of Smith & Nephew's, Inc.'s Motion for Partial Summary Judgment of Invalidity of Claims 10-12 of U.S. Patent No. 6,623,486. Sep. 10, 2008.

*Synthes (U.S.A.)* v. *Smith & Nephew, Inc.*, 03-0084 (E.D. Pa.). Declaration of David Seligson, M.D. in Support of Smith & Nephew's [sic], Inc.'s Motion for Partial Summary Judgment of Invalidity of Claims 10-12 of U.S. Patent No. 6,623,486. Sep. 10, 2008.

*Synthes (U.S.A.)* v. *Smith & Nephew, Inc.*, 03-0084 (E.D. Pa.). Expert Report of John F. Witherspoon. Apr. 9, 2008.

*Synthes (U.S.A.)* v. *Smith & Nephew, Inc.*, 03-0084 (E.D. Pa.). Initial Expert Report of J. Lawrence Marsh, M.D. Regarding the Invalidity of the Patents-in-Suit. Apr. 9, 2008.

*Synthes (U.S.A.)* v. *Smith & Nephew, Inc.*, 03-0084 (E.D. Pa.). Memorandum and Order. Feb. 4, 2008.

*Synthes (U.S.A.)* v. *Smith & Nephew, Inc.*, 03-0084 (E.D. Pa.). Second Supplement to Apr. 9, 2008 Expert Report of J. Lawrence Marsh, M.D. Sep. 3, 2008.

*Synthes (U.S.A.)* v. *Smith & Nephew, Inc.*, 03-0084 (E.D. Pa.). Second Supplement to Apr. 9, 2008 Expert Report of David Seligson, M.D, Sep. 5, 2008.

*Synthes (U.S.A.)* v. *Smith & Nephew, Inc.*, 03-0084 (E.D. Pa.). Second Supplement to Apr. 9, 2008 Expert Report of J. Lawrence Marsh, M.D. Sep. 3, 2008.

*Synthes (U.S.A.)* v. *Smith & Nephew, Inc.*, 03-0084 (E.D. Pa.). Smith & Nephew's Memorandum in Support of Its Motion for Partial Summary Judgment of Noninfringement of Claims 1, 6, 14, and 15 of U.S. Patent No. 6,623,486. Sep. 10, 2008.

*Synthes (U.S.A.)* v. *Smith & Nephew, Inc.*, 03-0084 (E.D. Pa.). Smith & Nephew's Memorandum in Support of Its Motion for Partial Summary Judgment of Invalidity of Claims 10-12 of U.S. Patent No. 6,623,486, Sep. 10, 2008.

*Synthes (U.S.A.)* v. *Smith & Nephew, Inc.*, 03-0084 (E.D. Pa.). Smith & Nephew's Memorandum in Support of Its Opposition to Synthes' Motion for Summary Judgment of No Invalidity of the Weaver Patents over the K982222 Reference. Sep. 29, 2008.

*Synthes (U.S.A.)* v. *Smith & Nephew, Inc.*, 03-0084 (E.D. Pa.). Smith & Nephew, Inc.'s Opening Brief in Support of Its Claim Constructions. Mar. 16, 2007.

*Synthes (U.S.A.)* v. *Smith & Nephew, Inc.*, 03-0084 (E.D. Pa.). Smith & Nephew, Inc.'s Responsive Brief in Support of Its Claim Construction. Apr. 20, 2007.

*Synthes (U.S.A.)* v. *Smith & Nephew, Inc.*, 03-0084 (E.D. Pa.). Supplement to Apr. 9, 2008 Expert Report of J. Lawrence Marsh, M.D. May 14, 2008.

*Synthes (U.S.A.)* v. *Smith & Nephew, Inc.*, 03-0084 (E.D. Pa.). Supplement to Expert Report of John F. Witherspoon. May 14, 2008.

*Synthes (U.S.A.)* v. *Smith & Nephew, Inc.*, 03-0084 (E.D. Pa..). "Declaration of Kristin J. Doyle in Support of Smith & Nephew's Opposition to Synthes' Motion for Summary Judgment of No Invalidity of the Weaver Patents Over the K982222 Reference.", Sep. 29, 2008.

The Titanium Distal Radius Plate: Technique Guide. Synthes (USA), 1997.

The Titanium Distal Radius Plate: Technique Guide. Synthes (USA), 1994.

Vattolo, Mauro. "The Effect of Grooves in Osteosynthesis Plates on the Restructuring of the Corticalis." Diss. University of Bern, Switzerland, 1986.

Weaver et al. U.S. Appl. No. 09/660,287: Bone Plating System. Information Disclosure Statement Under 37 C.F.R. § 1.97 and § 1.98. Nov. 13, 2000.

Weaver et al. U.S. Appl. No. 09/660,287: Bone Plating System. Second Information Disclosure Statement Under 37 C.F.R. § and § 1.98. Jan. 11, 2001.

Weaver et al. U.S. Appl. No. 09/660,287: Bone Plating System. Third Information Disclosure Statement Under 37 C.F.R. § 1.97 and § 1.98. Feb. 16, 2001.

Witten, Celia M. Letter to Sheri L. Musgnung (Synthes (USA)) Regarding Section 501(k) Notification of Intent to Market Distal Femur Plate System. Jul. 29, 1998.

\* cited by examiner

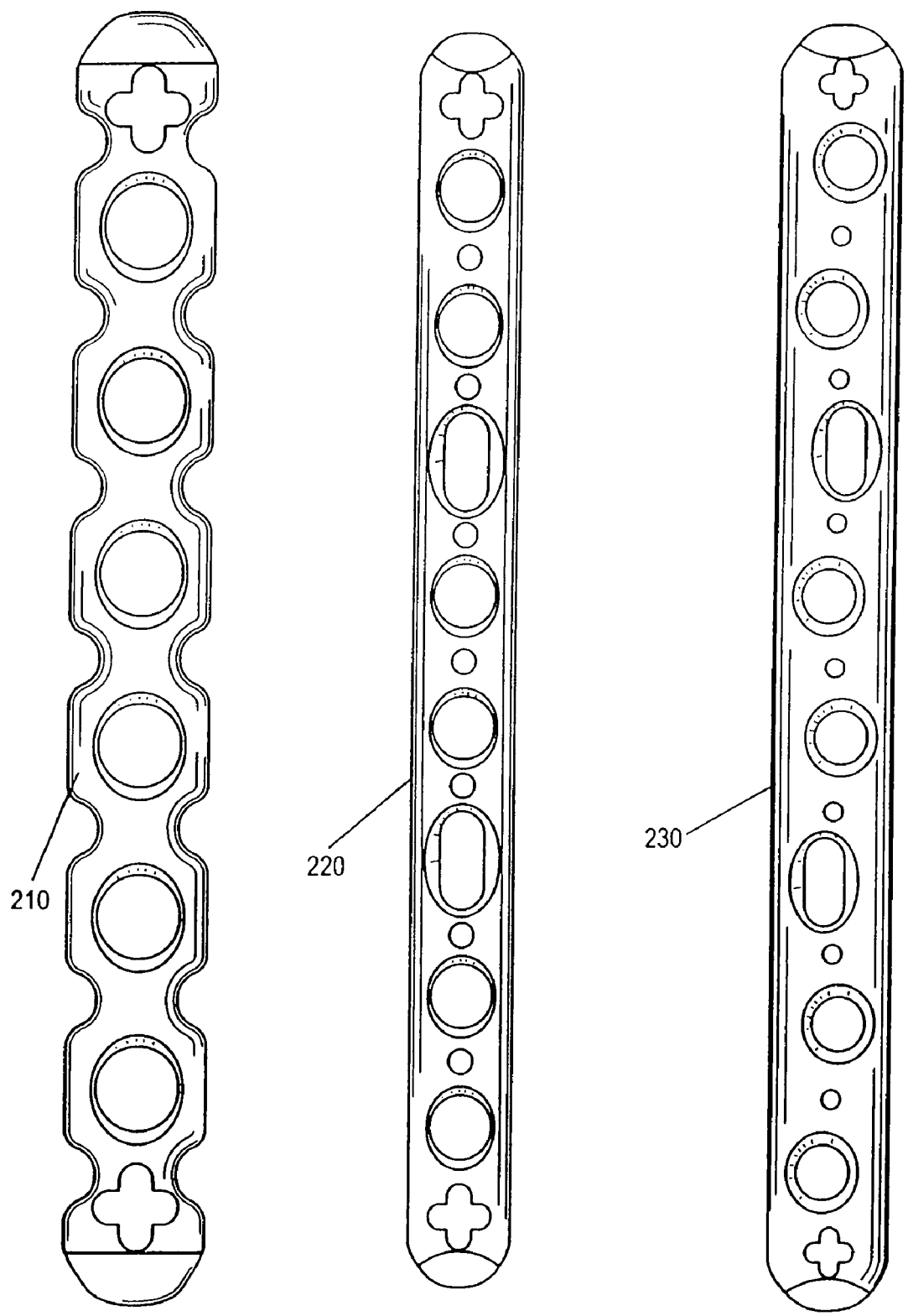
*Fig. 21*   *Fig. 22*   *Fig. 23*

BONE PLATE SYSTEMS USING PROVISIONAL FIXATION

This application is a continuation application of U.S. application Ser. No. 10/952,047, filed Sep. 28, 2004, now abandoned, which is a continuation-in-part application of U.S. application Ser. No. 10/673,833, filed Sep. 29, 2003 now U.S. Pat. No. 7,179,260, the entire contents of each of which are hereby incorporated by reference.

FIELD OF THE INVENTION

The invention relates generally to apparatuses for fixation of parts of a fractured bone, and, more particularly, to bone plates and bone plate assemblies for stabilization and compression of parts of a fractured bone and provisional fixation using holes in bone plates.

BACKGROUND OF THE INVENTION

Bone fractures lead to complex tissue injuries involving both the bone and the surrounding soft tissue. Treated in a conservative way, fractures often result in malalignment or non-unions and may also lead to stiffness of adjacent joints. To reduce the occurrence of these problems, open reduction and internal fixation of the bone can be carried out. Anatomical reduction and stable internal fixation with plates and screws are very successful in treating bone fractures.

Good bone healing can also result from relative stability, where the clinical outcome is often dependent on obtaining correct length, axis, and rotation of the fractured bone rather than on precise anatomical reduction and absolute stability. To achieve this, while at the same time minimizing the amount of additional soft tissue trauma, treatment of multifragmented metaphyseal and diaphyseal fractures with plates and screws was developed.

An existing solution is plate and screw systems where the screws are locked in the plate. The plate and screws form one stable system and the stability of the fracture is dependent upon the stiffness of the construct. No compression of the plate onto the bone is required, which reduces the risk of primary loss of reduction and preserves bone blood supply. Locking the screw into the plate to ensure angular, as well as axial, stability eliminates the possibility for the screw to toggle, slide, or be dislodged and thereby strongly reduces the risk of postoperative loss of reduction. As the relationship between the locking screws and the plate is fixed, locking screws provide a high resistance to shear or torsional forces, but locking screws have a limited capability to compress bone fragments.

Furthermore, existing plates with openings that accept locking screws typically only accept certain screw sizes with specified types of screw heads. For example, an existing plate and screw system includes a lag screw with a shallow thread form and a conical screw head. This limits the angulation of the screw, and the thread form is not optimal for lagging bone pieces together. This may be limiting in certain cases, for example with a distal femur fracture where a surgeon desires to lag the condyles. Because such existing plates do not accept large screws with spherical screw heads, surgeons are limited to lagging fragments outside the plate or using screws which are poorly designed for this application.

Because of these shortcomings, many surgeons began expressing the desire to have plate and screw systems (or bone plate assemblies) where the surgeon can choose intraoperatively whether to use the bone plate with compression screws (also referred to as cortical or cancellous screws), locking screws, or with a combination of both. This led to the development of a combination slot, a compression slot combined with a partially threaded opening, that could receive either a compression screw or a locking screw.

Bone plate assemblies that combine compression screws and locking screws are ideal in certain clinical situations. Bone plates with combination slots, including partially threaded openings, are well known to those skilled in the art. The partially threaded portions allow either locking or compression screws to be used. Because the slots are only partially threaded, the locking screws may not be able to maintain the fixed angular relationship between the screws and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intraoperative plate orientation. Because of the slot geometry, translation of the plate with compression screws may be limited to a single direction, which may be disadvantageous in reduction and manipulation of fragments.

Additionally, bone plates that allow for a surgeon to use provisional fixation techniques are also desirable. Provisional fixation of a bone plate to the bone allows the surgeon to fix the plate to the bone without the use of clamps or similar tools. In this way, the surgeon may place the bone plate in the proper position before inserting all of the locking screws into the bone plate and bone, while at the same time keeping excess instruments, such as clamps, out of the field of view of the surgeon and allowing for higher quality x-rays of the bone and bone plate construct during surgery.

Accordingly, there is a need for improved bone plates that may be used with both compression and locking screws for improved stabilization and compression of parts of a fractured bone. There is also a need for improved bone plates with holes that may be used for locking a bone plate to the bone, but that also accept different size screws with varying types of screw heads. Finally, there is need for improved bone plates that accept provisional fixation pins through the holes of the plate.

SUMMARY OF THE INVENTION

The present invention provides bone plates and bone plate assemblies for stabilization and compression of parts of a fractured bone. According to an exemplary embodiment of the present invention, a bone plate includes an upper surface, a bone contacting surface, and at least one hole extending through the upper surface and the bone contacting surface that may interchangeably receive a locking screw and a compression screw, wherein each hole includes a thread that makes a complete revolution around the hole.

According to an exemplary embodiment, a bone plate comprises an upper surface, a bone contacting surface, and a plurality of holes for receiving bone screws, wherein each hole extends through the upper surface and the bone contacting surface, may interchangeably receive a locking screw and a compression screw, and includes a thread that makes a complete revolution around the hole. Each hole may further include a top portion extending from the upper surface and a bottom threaded portion extending from the top portion to the bone contacting surface. The bottom portion may be tapered with an included angle of less than about thirty degrees. The threads of each hole may be configured to receive threads of a head of a locking screw. Each hole may be configured to threadably engage a head of a locking screw and fix the locking screw with respect to the bone plate. Each hole may be configured to engage a head of a compression screw and provide compression of fractured bone fragments.

An exemplary embodiment of a method of reducing a bone fracture comprises inserting a provisional fixation pin through a first hole in a bone plate to couple the bone plate to the bone, wherein the first hole is one of a plurality of holes in the bone plate for receiving bone screws, drilling a hole in the bone through a second hole of the plurality of holes, and inserting a locking screw through the second hole and into engagement with the bone to fix the position of the bone plate. One or more additional provisional fixation pins may be inserted through one or more additional holes of the plurality of holes before or after drilling a hole in the bone. Each hole of the plurality of holes in the bone plate may interchangeably receive a locking screw and a compression screw and includes a thread that makes a complete revolution around the hole.

Another exemplary embodiment of a method of reducing a fracture of a bone comprises inserting a provisional fixation pin through a first hole in a bone plate to couple the bone plate to the bone, wherein the first hole is one of a plurality of holes in the bone plate for receiving bone screws, drilling a hole in the bone through a second hole of the plurality of holes, and inserting a compression screw through the second hole and into engagement with the bone to lag a bone fragment to the bone plate. Another hole may be drilled in the bone through a third hole of the plurality of holes and a locking screw inserted through the third hole and into engagement with the bone to fix the position of the bone plate. One or more additional provisional fixation pins may be inserted through one or more additional holes of the plurality of holes before or after drilling a hole in the bone. Each hole of the plurality of holes in the bone plate may interchangeably receive a locking screw and a compression screw and includes a thread that makes a complete revolution around the hole.

An exemplary embodiment of a bone plate assembly comprises a bone plate, at least one locking screw, at least one compression screw, and at least one provisional fixation pin. The bone plate includes an upper surface, a bone contacting surface, and a plurality of holes for receiving bone screws, wherein each hole extends through the upper surface and the bone contacting surface, may interchangeably receive a locking screw and a compression screw, and includes a thread that makes a complete revolution around the hole. The at least one provisional fixation pin may be received within at least one of the plurality of holes for receiving bone screws. The bone plate assembly may also include other provisional fixation pins that are to be used in pinholes that may be present in the bone plate, such that the bone plate assembly includes provisional fixation pins for use with both pinholes and other provisional fixation pins separately for use with holes for receiving bone screws.

Other exemplary embodiments of this invention include bone plates, bone plate assemblies, and methods of fracture reduction and provisional fixation further described herein and in co-pending U.S. application Ser. No. 10/673,833, which is incorporated herein by reference.

BRIEF DESCRIPTION OF THE DRAWINGS

FIGS. 10-27 are perspective views of various exemplary bone plate configurations according to various embodiments of the present invention.

DETAILED DESCRIPTION OF THE INVENTION

The present invention provides bone plates and bone plate assemblies for stabilization and compression of parts of a fractured bone. According to certain exemplary embodiments of this invention, a bone plate includes an upper surface, a bone contacting surface, and at least one hole extending through the upper surface and the bone contacting surface that may interchangeably receive a locking screw and a compression screw. The bone plate may include additional openings that receive only compression screws or only locking screws. The bone plate may also include pinholes that accept provisional fixation pins, but that are not large enough to receive bone screws.

A threaded head of an exemplary locking screw for use in accordance with this invention is received by threads in a corresponding hole such that the threads of the hole completely surround the threads of the head of the locking screw. This relationship between the head of the locking screw and the threads of the hole contributes to maintaining fixation of the bone plate and strengthening the plate and screw combination. As noted, a compression screw may also be received within the hole of the bone plate. As the compression screw is fully inserted within a bone, the head of the compression screw comes into contact with and rides along a top portion of the hole, allowing for fine adjustment of the position of the bone plate in more than one direction.

Figure 1A:
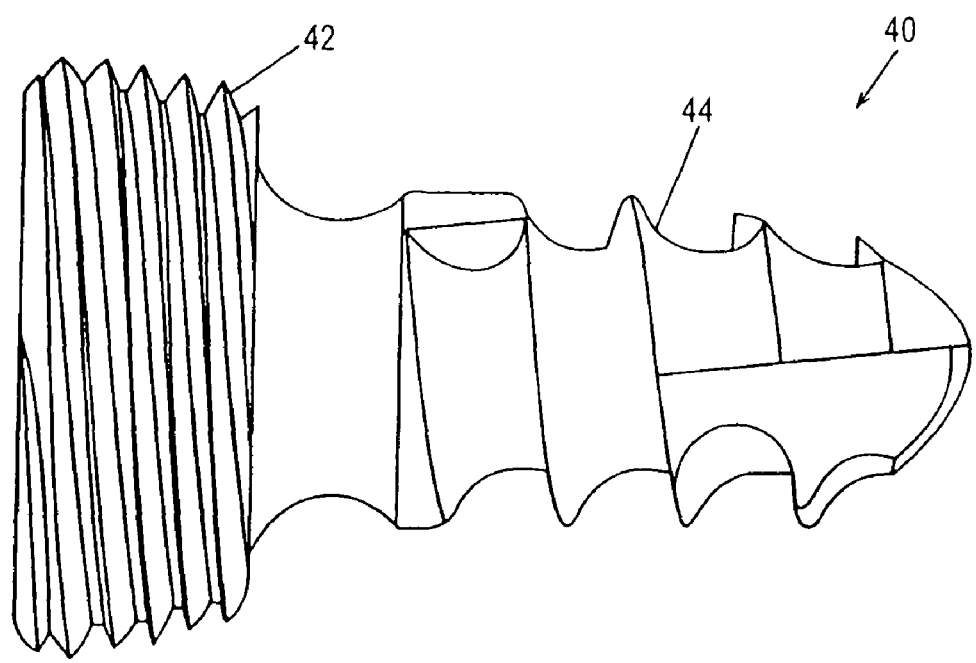
FIG. 1A shows a side view of an exemplary locking screw according to one embodiment of the present invention.
Figure 1B:
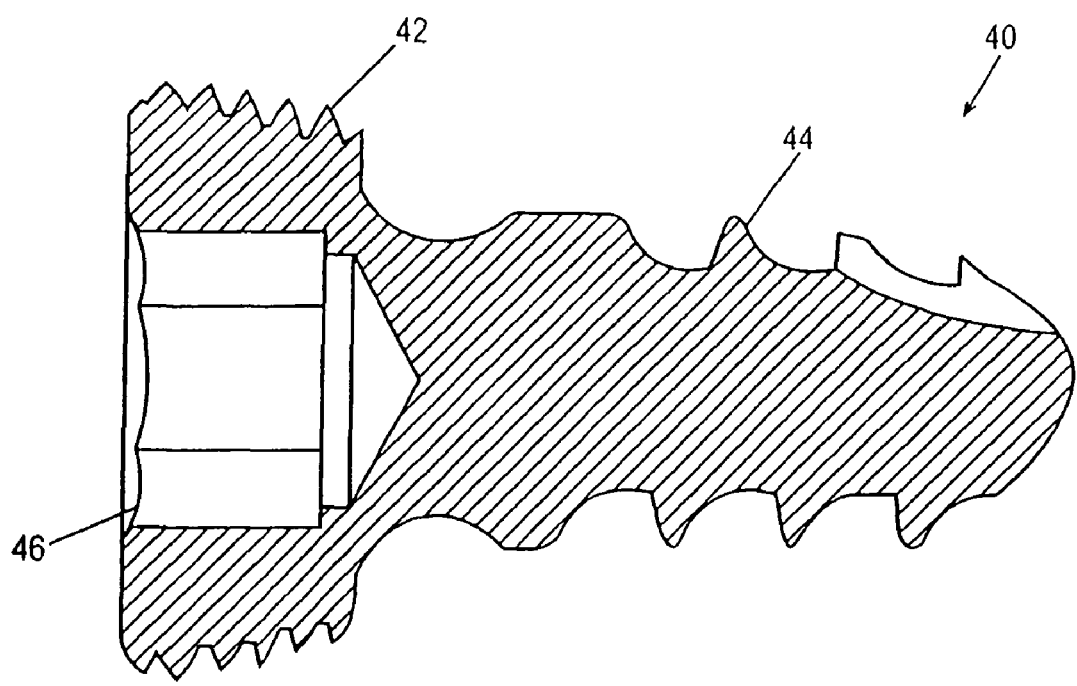
FIG. 1B shows a cross-sectional view of the locking screw of FIG. 1A.

FIGS. 1A and 1B show an exemplary locking screw for use according to one embodiment of the present invention. A locking screw 40 includes a threaded head 42 and a threaded shaft 44. Locking screw 40 may be a 3.5 mm, 4.5 mm, 6.5 mm, or other size locking screw, which is understood by those skilled in the art. In the exemplary embodiment shown in FIGS. 1A and 1B, the lead between the threads of head 42 and the threads of shaft 44 is broken. The threads in shaft 44 of locking screw 40 are single lead and the threads in head 42 are triple lead, providing locking screw 40 with same pitch throughout. It is preferable for certain embodiments of locking screws according to this invention to have a constant pitch. In an exemplary 3.5 mm locking screw, the pitch is 1.25 mm and the angle of the thread form is about 45 to about 60 degrees. In an exemplary 4.5 mm locking screw, the pitch is 1.75 mm and the angle of the thread form is about 60 degrees. Locking screw 40 also includes an internal hex head 46, as shown in FIG. 1B, that is used when tightening locking screw 40 into a bone plate and/or bone.

FIGS. 2A-2E show different views of a portion of a bone plate according to an embodiment of the present invention. For ease of illustration and for purposes of describing an exemplary embodiment of the present invention, only a portion of bone plate 50 is shown in FIGS. 2A-2E. Bone plates generally include one or more holes or other openings, including pinholes that cannot receive bone screws, such as in the exemplary bone plates shown in FIGS. 10-27 and 29-33, which are briefly described below. For example, the bone plates shown in FIGS. 27 and 29-33 include only holes of the type described herein that may receive either locking screws or compression screws interchangeably. These bone plates also include non-threaded pinholes that may receive provisional fixation pins, but that cannot receive bone screws. As other examples, the bone plates shown in FIGS. 10-26 generally include holes of the type described herein that may receive either locking screws or compression screws interchangeably, as well as other oblong or non-threaded openings for receiving bone screws. These bone plates may also include cross-shaped slots or pinholes for receiving provisional fixation pins as well.

Figure 2A:
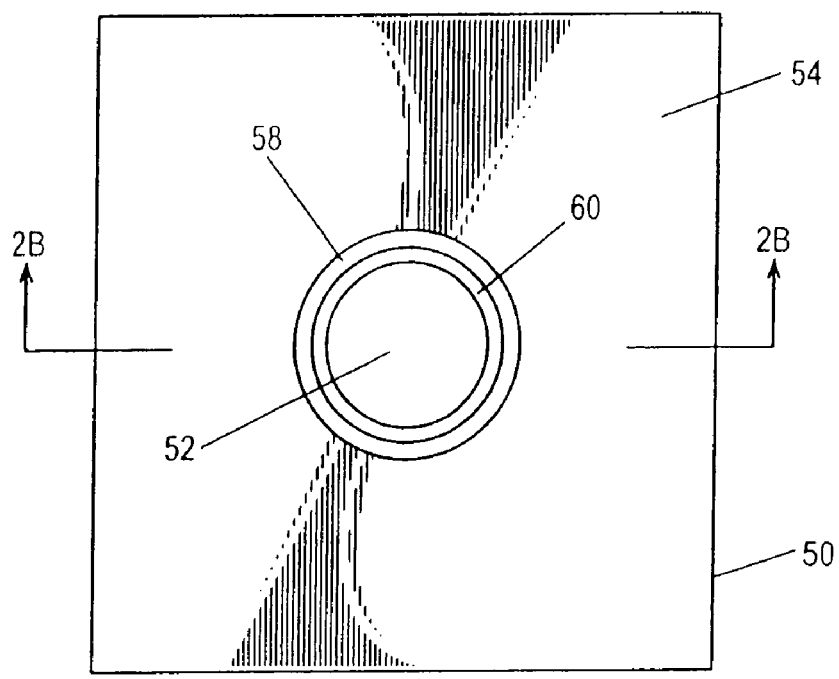
FIG. 2A shows a top view of a portion of a bone plate, including a hole without the threads of the hole shown, according to one embodiment of the present invention.
Figure 2B:
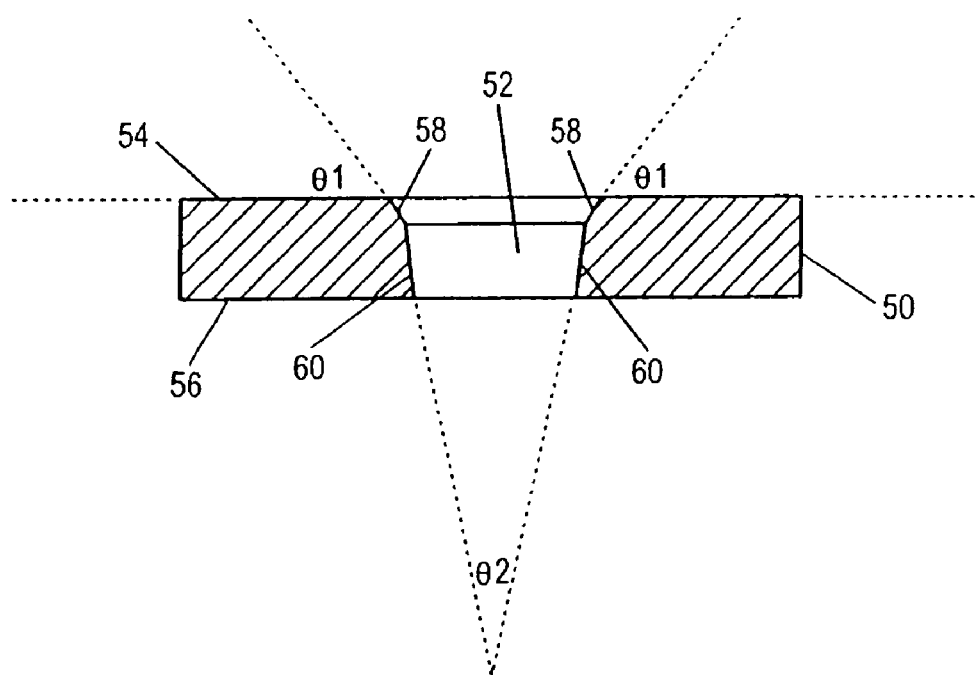
FIG. 2B shows a cross-sectional view of the portion of the bone plate shown in FIG. 2A as viewed along cross-section lines 2B-2B of FIG. 2A.
Figure 2C:
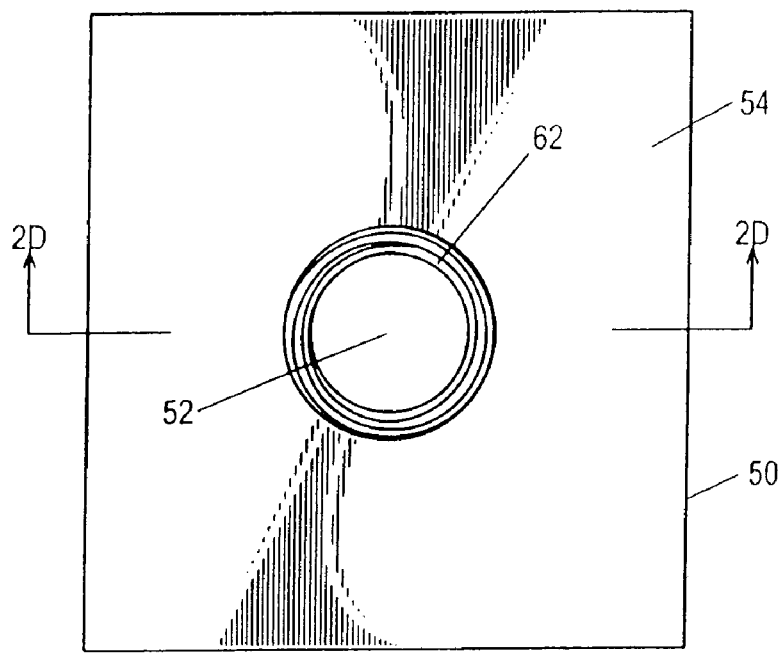
FIG. 2C shows a top view of the portion of the bone plate shown in FIGS. 2A and 2B, with the threads of the hole shown.
Figure 2D:
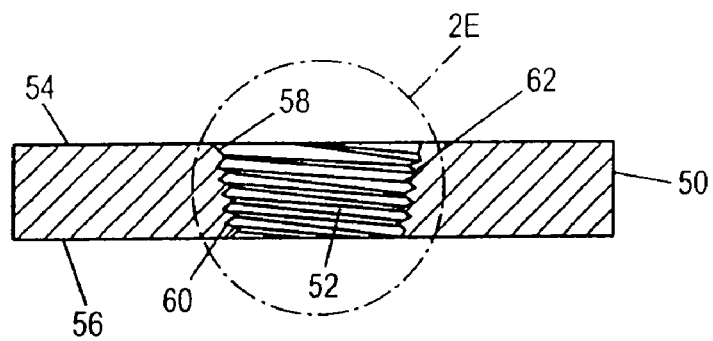
FIG. 2D shows a cross-sectional view of the portion of the bone plate shown in FIGS. 2A-2C as viewed along cross-section lines 2D-2D of FIG. 2C.
Figure 2E:
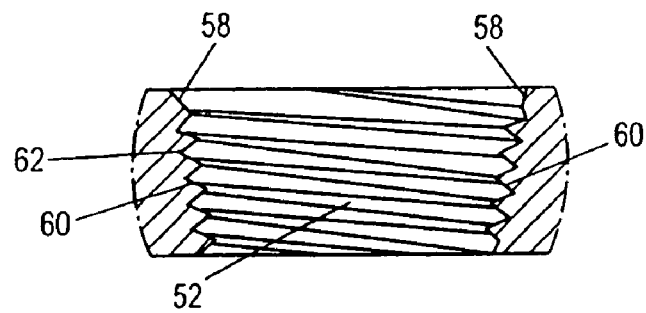
FIG. 2E shows a detailed view of the hole of the portion of the bone plate shown in FIGS. 2A-2D.

The particular bone plate 50 shown in these drawings includes a hole 52 extending through an upper surface 54 and a bone contacting surface 56 of bone plate 50. FIGS. 2A and 2B show hole 52 without its threads to help illustrate certain aspects of this embodiment of the invention, while FIGS. 2C-2E show hole 52 with its threads. It should be understood that the geometry of hole 52 is the same throughout these drawings, although the geometry of hole 52 is not as clearly visible in the drawings that show the threads of hole 52. As seen most clearly in FIG. 2B, hole 52 includes a top portion 58 extending downward from upper surface 54. Top portion 58 is generally frustoconical in shape and extends from upper surface 54 at an angle of θ1 relative to the plane of top surface 54, as shown in FIG. 2B. In an exemplary embodiment, angle θ1 is about fifty-two degrees.

A bottom portion 60 of hole 52 extends from the end of top portion 58 through bone contacting surface 56 of bone plate 50. Bottom portion 60 includes threads 62, as shown in FIGS. 2C-2E. Some of threads 62 may extend into top portion 58 depending on the particular embodiment, but top portion 58 is not completely threaded.

In the exemplary embodiment shown in FIGS. 2A-2E, bottom portion 60 is tapered. The included angle, θ2 shown in FIG. 2B, of the taper of bottom portion 60 may be less than about thirty degrees, including zero degrees (i.e., no taper at all). The larger the included angle, the larger hole 52 in bone plate 50 must be, which begins to compromise the strength of the plate if the included angle is much larger than about thirty degrees. In an exemplary embodiment, θ2 is about twenty degrees.

Figure 3:
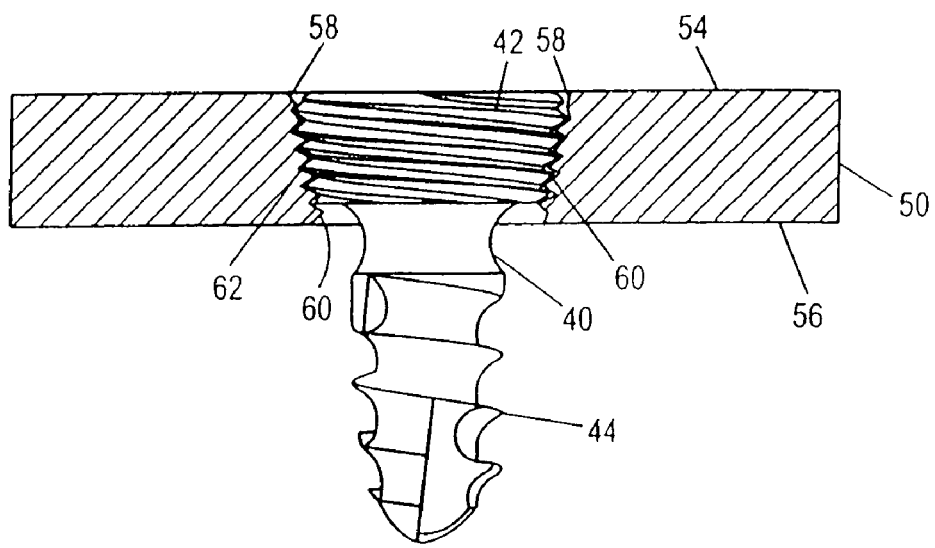
FIG. 3 shows a side view of the locking screw of FIGS. 1A and 1B threaded into the portion of the bone plate shown in FIGS. 2A-2E.

FIG. 3 shows a side view of locking screw 40 threaded into hole 52 of bone plate 50. Head 42 of locking screw 40 is received by threads 62 of bone plate 50. Threads 62 completely surround the threads of head 42, and the top of head 42 is received completely within hole 52 such that head 42 of locking screw 40 sits flush with upper surface 54 of bone plate 50. Shaft 44 of locking screw 40 is threaded into bone (not shown). Head 42 of locking screw 40 should be tapered such that it properly mates with threads 62 of hole 52 of bone plate 50. Furthermore, a threaded portion of a head of a locking screw for use with certain embodiments of this invention should have a taper generally corresponding to the taper, if any, of the threads of the hole of the bone plate.

Figure 4:
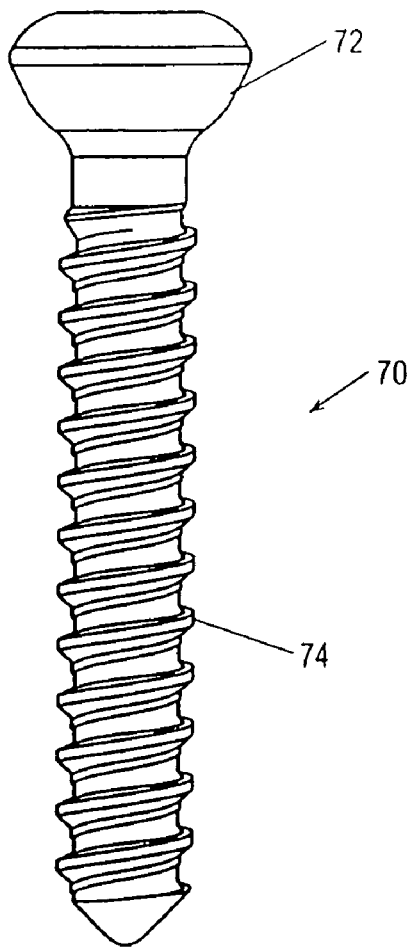
FIG. 4 shows a side view of an exemplary compression screw for use according to one embodiment of the present invention.
Figure 5:
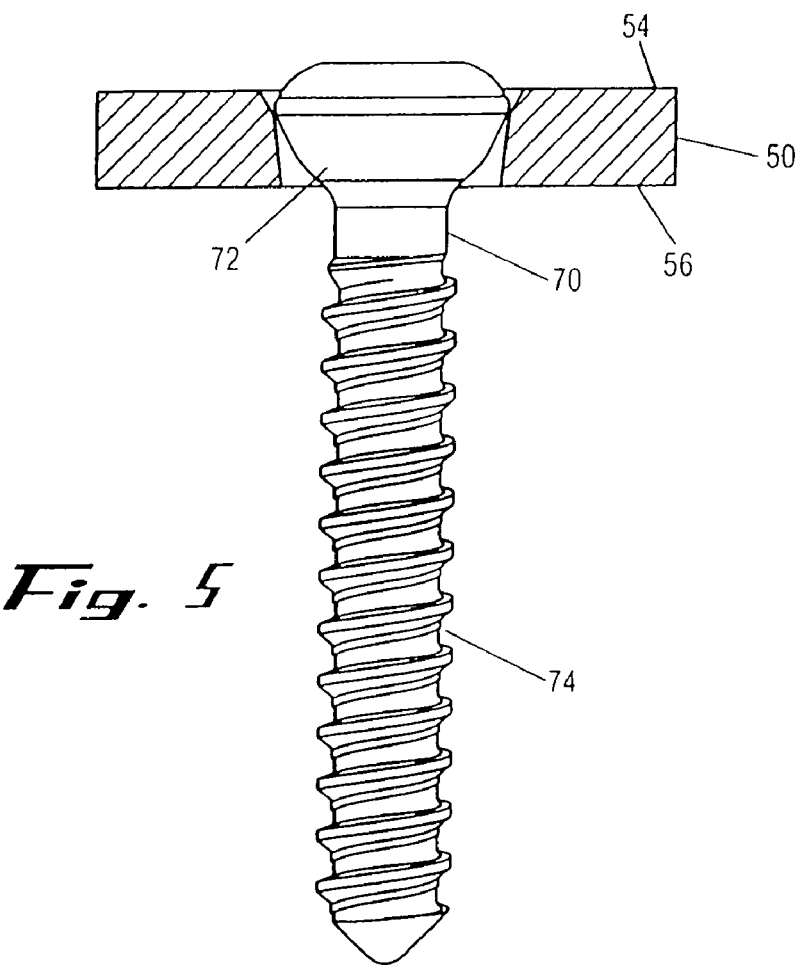
FIG. 5 shows a side view of the compression screw of FIG. 4 inserted into the portion of the bone plate shown in FIGS. 2A-2E.

FIG. 4 shows a side view of an exemplary compression screw for use according to an embodiment of the present invention. A compression screw 70 includes a head 72 and a threaded shaft 74 for engaging a bone. Head 72 is preferably spherical, as shown in the drawings. FIG. 5 shows compression screw 70 inserted within hole 52 of bone plate 50. As shown in FIG. 5, head 72 of compression screw 70 rides along top portion 58 of bone plate 50. As shown clearly in FIG. 5, the diameter of shaft 74 is less than the diameter of the opening at bottom portion 60 of hole 52. Thus, as shaft 74 is threaded into a bone (not shown), compression screw 70 may pull or push bone plate 50 in a particular direction as the spherical head 72 of compression screw 70 comes into contact with and rides along the frustoconical top portion 58 of hole 52 of bone plate 50. The angle θ1, shown in FIG. 2B, at top portion 58 of hole 52 is significant for compression of a fracture and is necessary to help shift the bone plate in the desired direction. If top portion 58 were to extend straight down from upper surface 54 of bone plate 50, compression would be less successful. Compression screw 70 may move bone plate 50 in more than one direction as compression screw 70 is fully inserted within hole 52. In an exemplary embodiment, fine adjustment of fractures up to about two millimeters in several directions is possible.

Figure 6A:
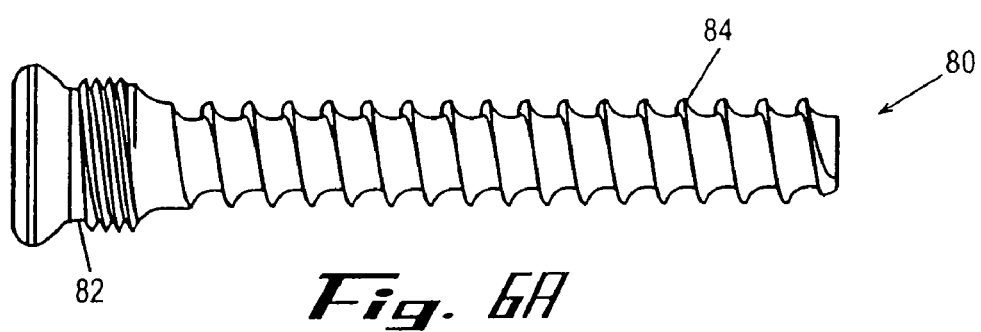
FIG. 6A shows a side view of an exemplary locking screw according to an embodiment of the present invention.
Figure 6B:
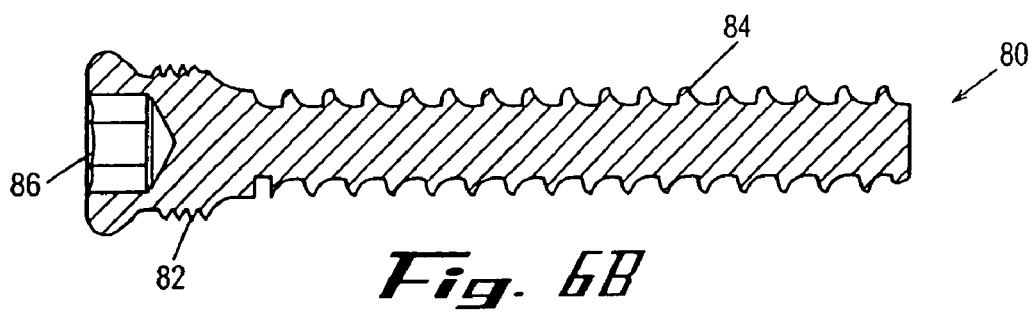
FIG. 6B shows a cross-sectional view of the locking screw of FIG. 6A.

FIGS. 6A and 6B show another exemplary locking screw for use according to an embodiment of the present invention. A locking screw 80 includes a head 82 and a threaded shaft 84. Similar to locking screw 40 shown in FIGS. 1A and 1B, locking screw 80 may be a 3.5 mm, 4.5 mm, 6.5 mm, or other size locking screw, which is understood by those skilled in the art, and the lead between the threads of head 82 and the threads of shaft 84 is broken. The threads in shaft 84 of locking screw 80 are single lead and the threads in head 82 are triple lead, providing locking screw 80 with the same pitch throughout. The pitches and angles of thread form for exemplary 3.5 and 4.5 mm locking screws 80 are generally similar to those described above with reference to locking screw 40.

Locking screw 80 also includes an internal hex head 86, as shown in FIG. 6B, that is used when tightening locking screw 80 into a bone plate and/or bone. As may be seen from FIGS. 1A, 1B, 6A, and 6B, only a portion of head 82 of locking screw 80 is threaded, whereas the entire head 42 of locking screw 40 is threaded. Additionally, the threaded portion of head 82 of locking screw 80 is not tapered, while head 42 of locking screw 40 is tapered. These differences are because locking screw 40 is designed to mate with hole 52 of bone plate 50, while locking screw 80 is designed to mate with a hole 92 of a bone plate 90, as further described below.

Figure 7A:
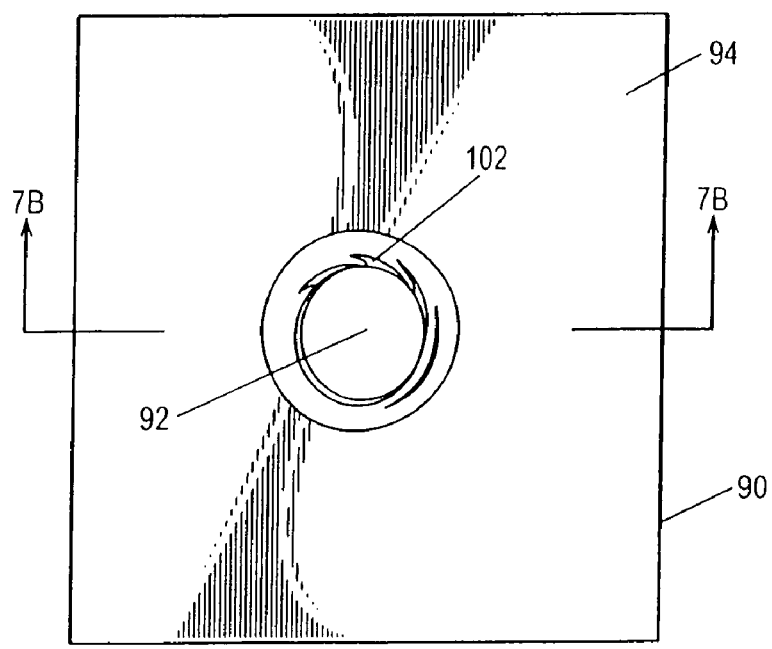
FIG. 7A shows a top view of a portion of a bone plate according to an embodiment of the present invention.
Figure 7B:
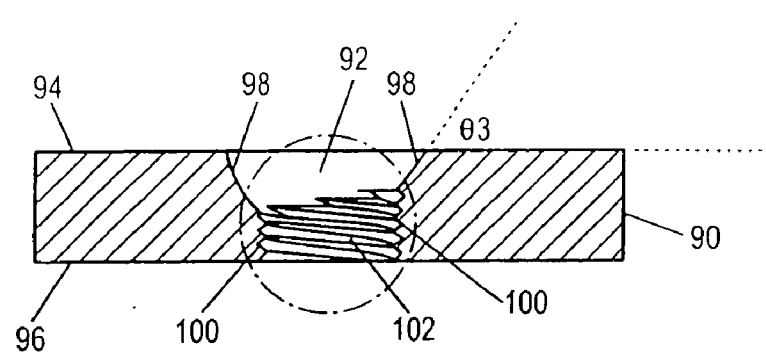
FIG. 7B shows a cross-sectional view of the portion of the bone plate shown in FIG. 7A as viewed along cross-section lines 7B-7B of FIG. 7A.
Figure 7C:
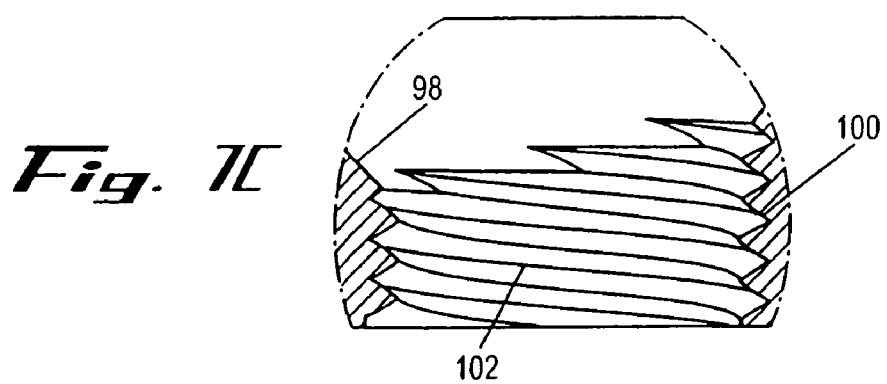
FIG. 7C shows a detailed view of the hole of the portion of the bone plate shown in FIGS. 7A and 7B.

FIGS. 7A-7C show different views of a portion of a bone plate according to an embodiment of the present invention. As noted above, bone plates generally include one or more holes or other openings, such as in the exemplary bone plates shown in FIGS. 10-27 and 29-33, but for ease of illustration, only a portion of bone plate 90 is shown in FIGS. 7A-7C.

Bone plate 90 includes a hole 92 extending through an upper surface 94 and a bone contacting surface 96 of bone plate 90. Hole 92 includes a top portion 98 extending downward from upper surface 94. As shown in FIG. 7B, one side of top portion 98 includes a ramp that extends from upper surface 94 at an angle of θ3 relative to the plane of top surface 94. In an exemplary embodiment, angle θ3 is about fifty-two degrees. The remainder of top portion 98 is a concave recessed portion that is generally spherical in shape, as shown in FIG. 7B. Although of a slightly different structure than top portion 58 of hole 52, top portion 98 of hole 92 also has a generally frustoconical shape, as shown in the figures.

A bottom portion 100 of hole 92 extends from the end of top portion 98 through bone contacting surface 96 of bone plate 90. Bottom portion 100 includes threads 102. Some of threads 102 may extend into top portion 98 depending on the particular embodiment, but top portion 98 generally has only the beginning of thread leads, if any threading. Bottom portion 100 is not tapered, but rather is generally cylindrical in shape. In certain embodiments, for example, bottom portion 60 of hole 52 of bone plate 50, bottom portion 100 may be tapered at an included angle of less than about thirty degrees.

Figure 8:
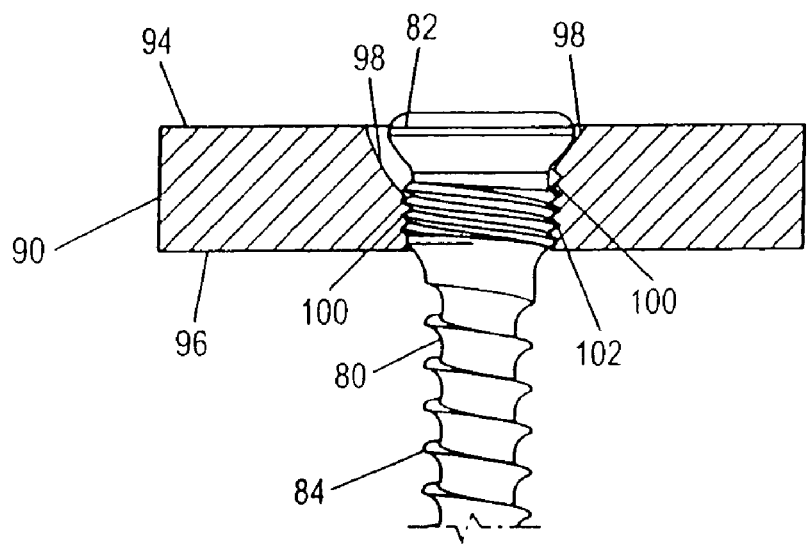
FIG. 8 shows a side view of the locking screw of FIGS. 6A and 6B threaded into the portion of the bone plate shown in FIGS. 7A-7C.

FIG. 8 shows a side view of locking screw 80 threaded into hole 92 of bone plate 90. Threads of head 92 of locking screw 90 are received by threads 102 of bone plate 90. Threads 102 completely surround the threads of head 92, and shaft 84 of locking screw 80 is threaded into bone (not shown). Head 82 of locking screw 80 is shaped such that its unthreaded portion bears against the ramp of top portion 98 of hole 92 of bone plate 90. Additionally, the threaded portion of head 82 is generally cylindrical (i.e., not tapered) so that it properly mates with threads 102 of hole 92 of bone plate 90. A threaded portion of a head of a locking screw for use with certain embodiments of this invention should be shaped to generally correspond to the shape of threaded portion of the hole of the bone plate.

Figure 9:
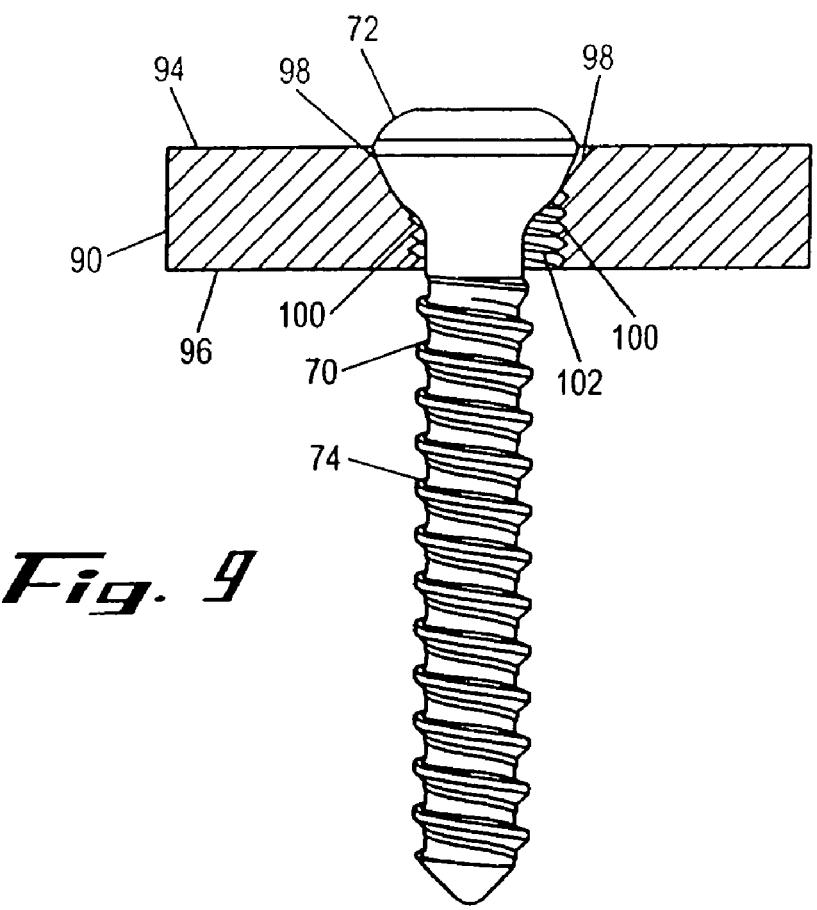
FIG. 9 shows a side view of the compression screw of FIG. 4 inserted into the portion of the bone plate shown in FIGS. 7A-7C.

FIG. 9 shows compression screw 70 inserted within hole 92 of bone plate 50. As shown in FIG. 9, head 72 of compression screw 70 sits within the frustoconical top portion 98, contacting the concave recessed area of top portion 98 of bone plate 90. Head 72 of compression screw 70 contacts the ramp area of top portion 98, but head 72 does not completely abut the ramp. As shown clearly in FIG. 9, the diameter of shaft 74 is less than the diameter of the opening at bottom portion 100 of hole 92. Thus, as shaft 74 is threaded into a bone (not shown), compression screw 70 may pull or push bone plate 90 in a particular direction as spherical head 72 of compression screw 70 comes into contact with and rides along the frustoconical top portion 98 of hole 92 of bone plate 90, similar to that described above with reference to FIG. 5. The angle θ3, shown in FIG. 7B, at top portion 98 of hole 92 is significant for compression of a fracture and is necessary to help shift the bone plate in the desired direction. If top portion 98 were to extend straight down from upper surface 94 of bone plate 90, compression would be less successful. Compression screw 70 may move bone plate 90 in more than one direction as compression screw 70 is fully inserted within hole 92. In an exemplary embodiment, fine adjustment of fractures up to about two millimeters in several directions is possible.

Certain exemplary embodiments of bone plates according to this invention include holes, such as hole 52 or hole 92, that not only receive compression or locking screws interchangeably but also accept multiple types of compression screw heads with varying outer and inner diameters and thread forms. A compression screw can be placed through such holes and use for fixation, provided the minor diameter of the screw shank does not exceed the minor diameter of the hole. The diameter of the head of the compression screw should not be less than the minor diameter of the hole because the compression screw would not then rest on any part of the bone plate as is necessary for fracture reduction.

FIGS. 10-26 show various exemplary bone plate configurations that may include one or more holes, such as holes 52 and 92 described above, that are capable of interchangeably receiving compression screws and locking screws. The exemplary bone plates shown in FIGS. 10-26 may also include other openings configured to receive only locking screws or only compression screws, which is well understood by those skilled in the art. The exemplary bone plates shown in FIGS. 10-26 may also include pinholes or provisional fixation slots that may receive provisional fixation pins. All holes in the exemplary plates of FIGS. 10-26 include threads (not shown), while the other generally non-circular openings in these plates may or may not include threads depending on the purposes for which the opening is to be used. Pinholes and provisional fixation slots are not threaded. The bone plates shown in FIGS. 10-26 are further described in co-pending and commonly-assigned U.S. application Ser. No. 10/673,833, entitled "Bone Plates and Bone Plate Assemblies," filed Sep. 29, 2003, which has been incorporated by reference herein in its entirety.

Figure 10:
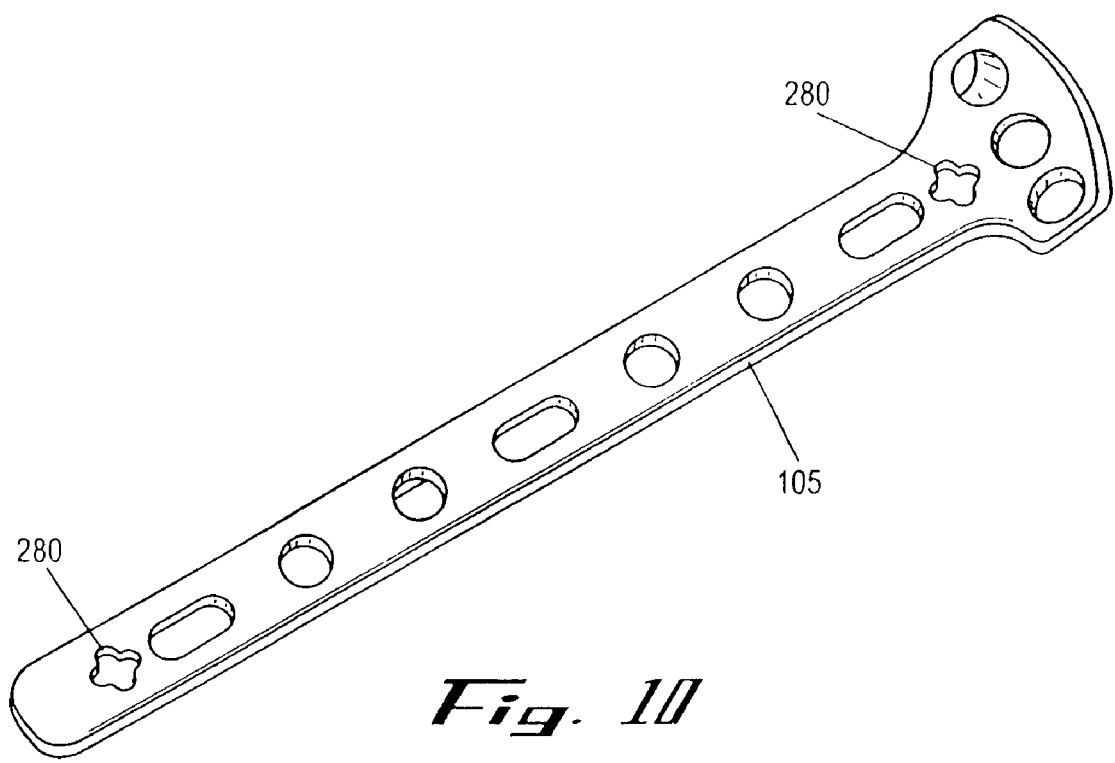
Figure 11:
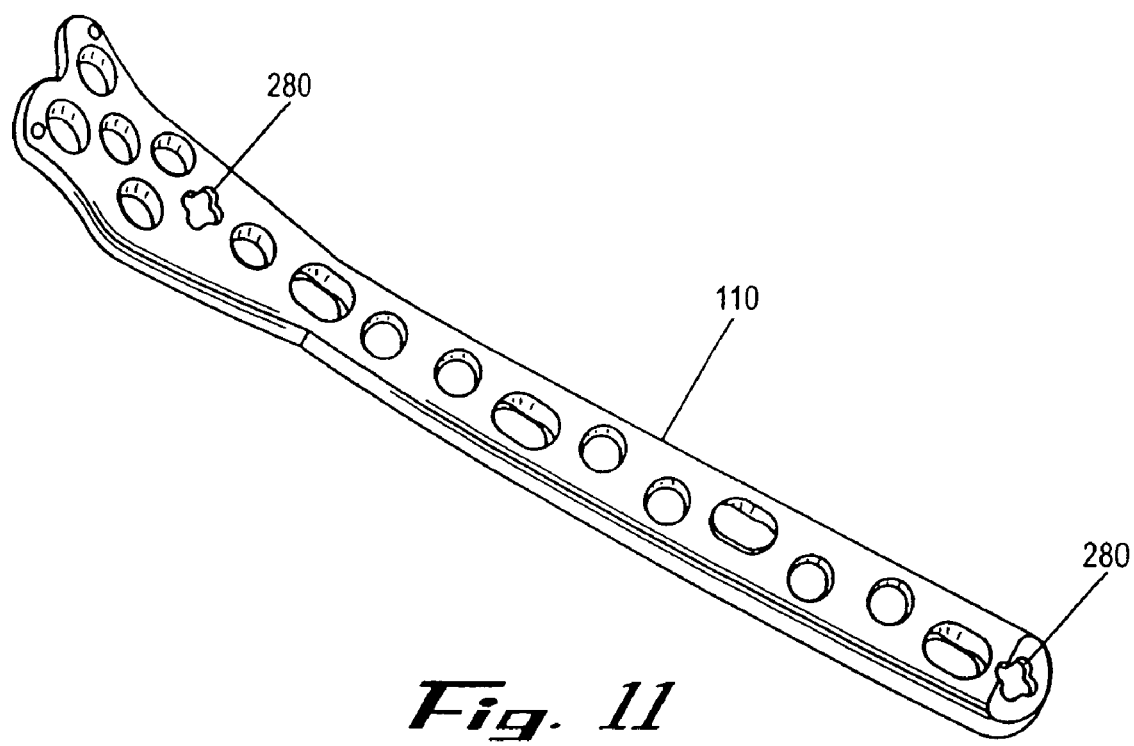
Figure 12:
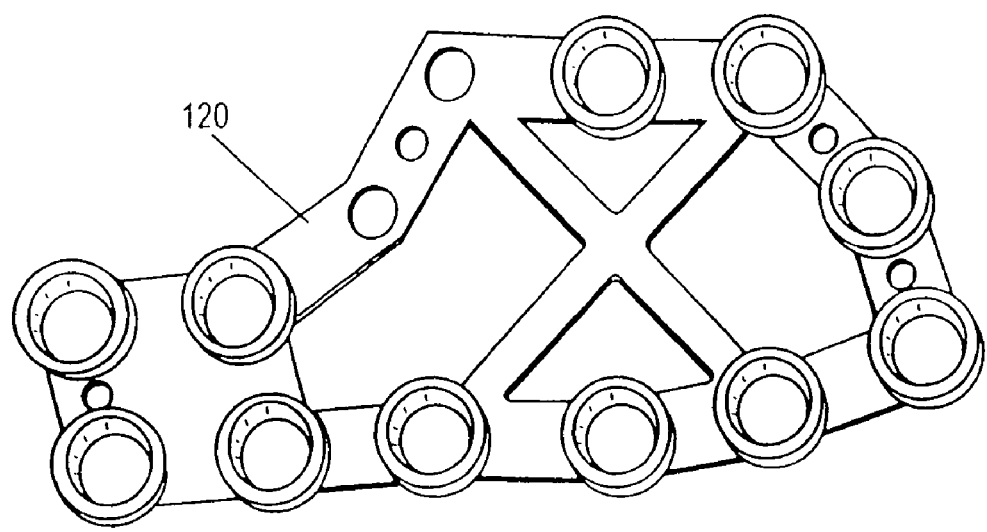
Figure 13:
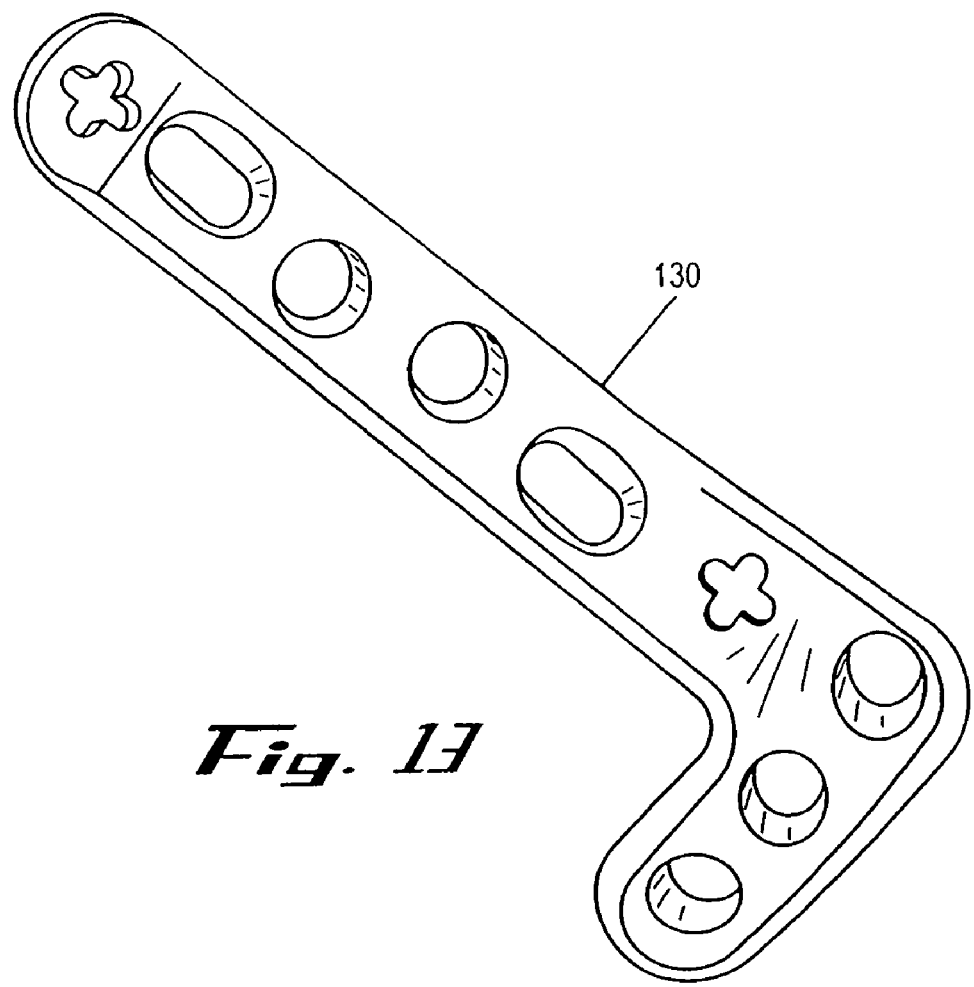
Figure 14:
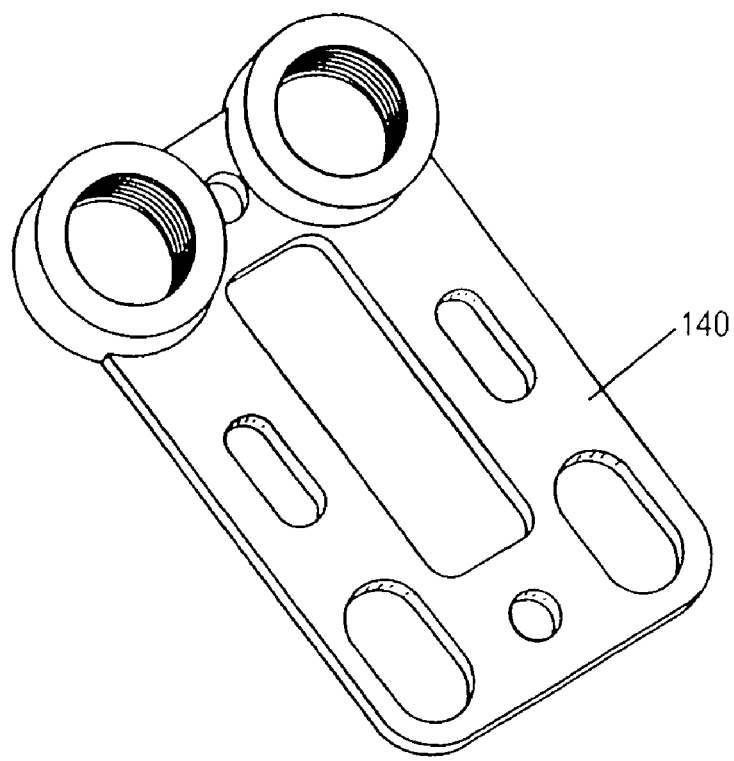
Figure 15:
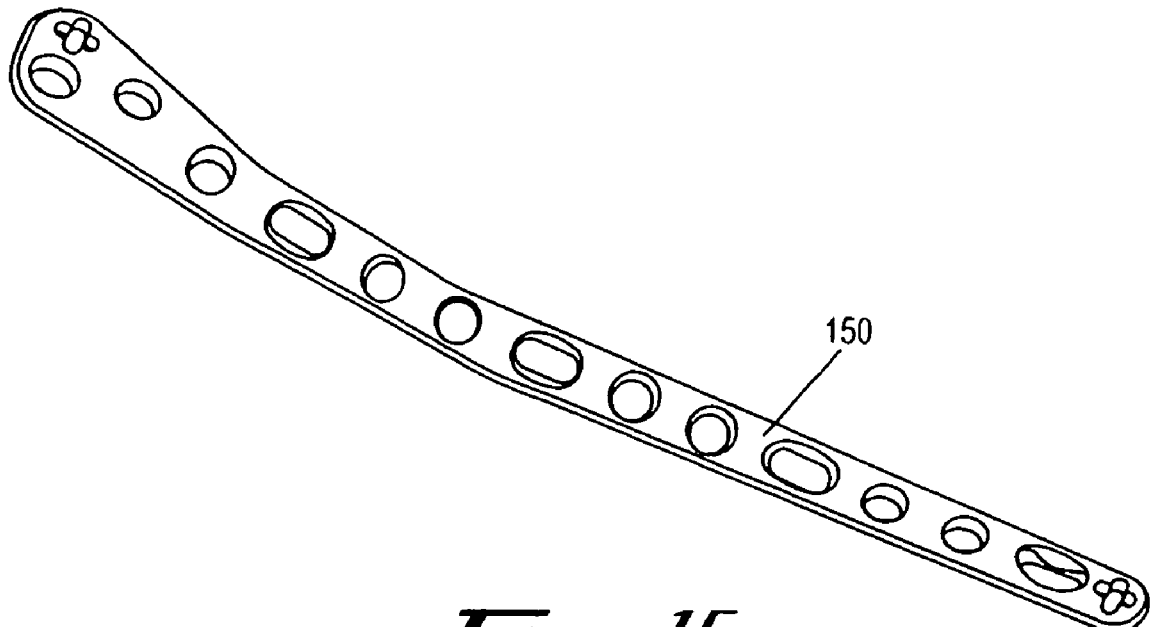
Figure 16:
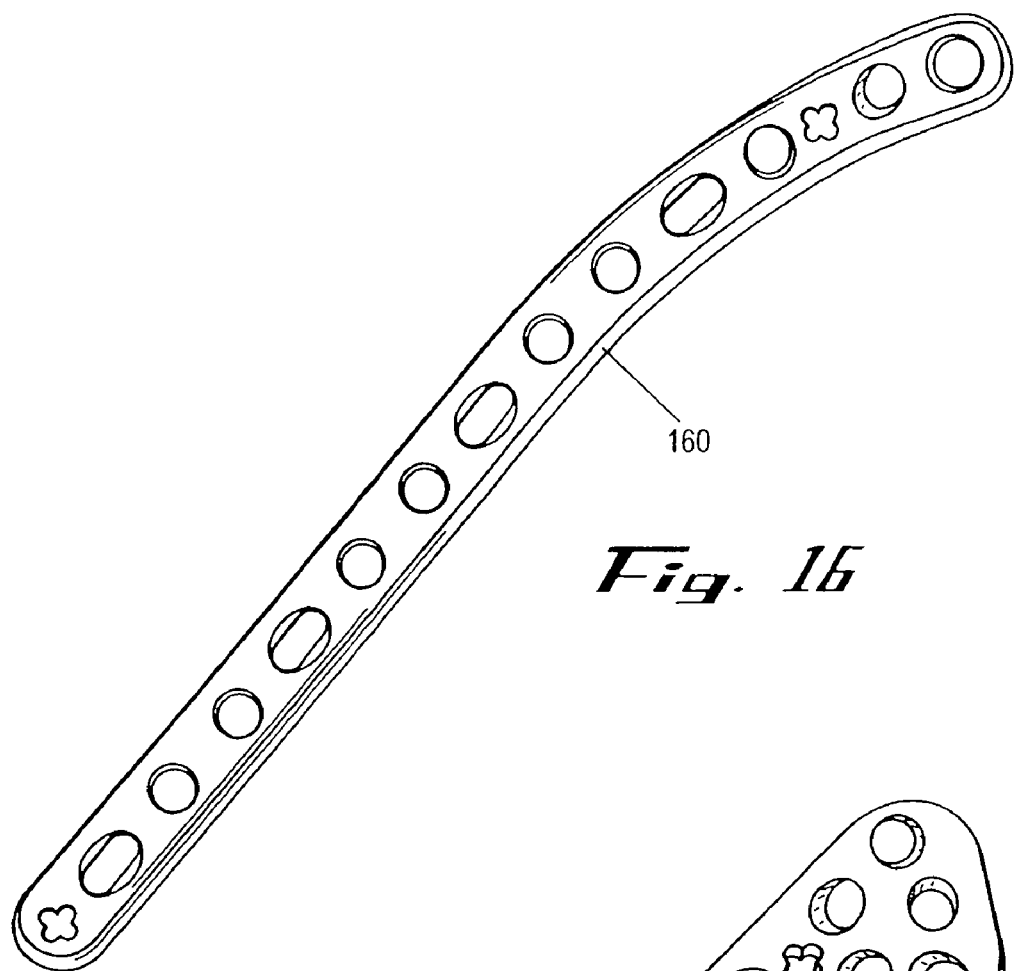
Figure 17:
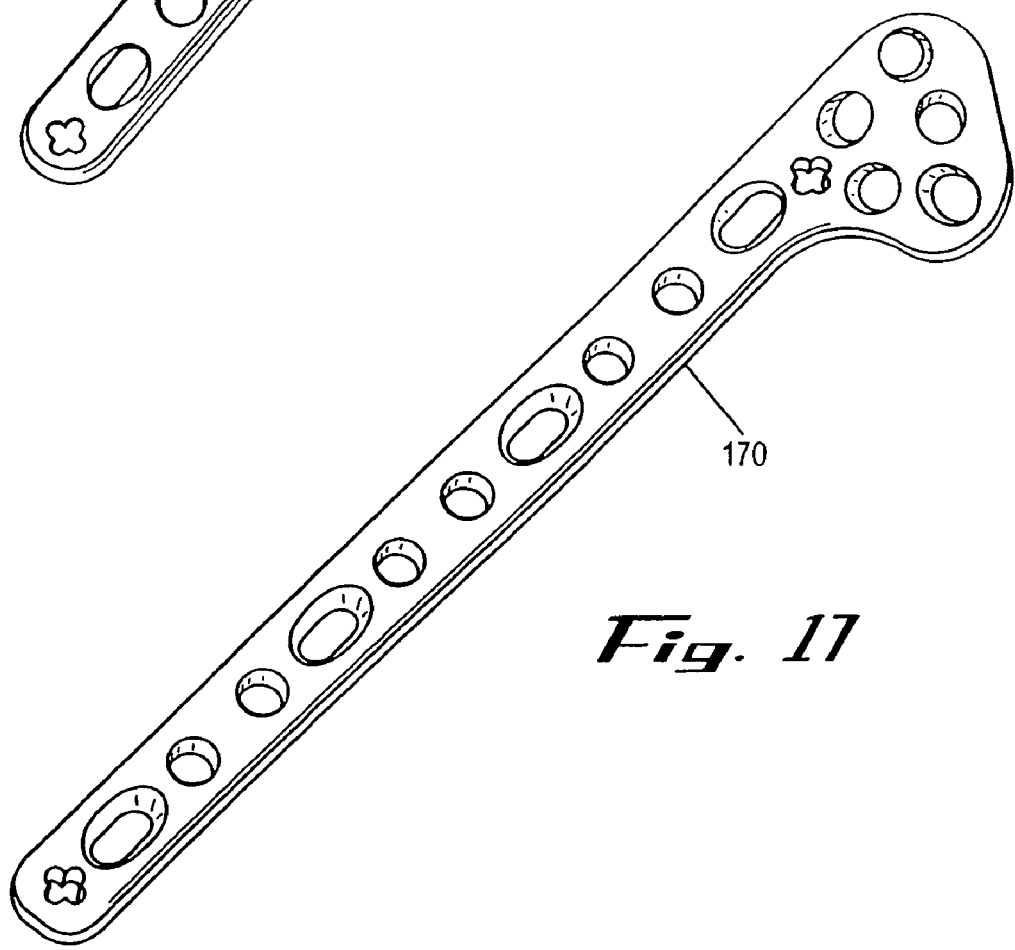
Figure 18:
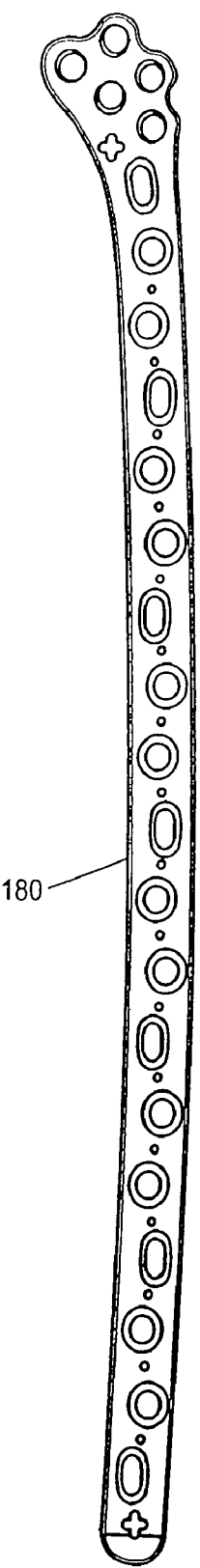
Figure 19:
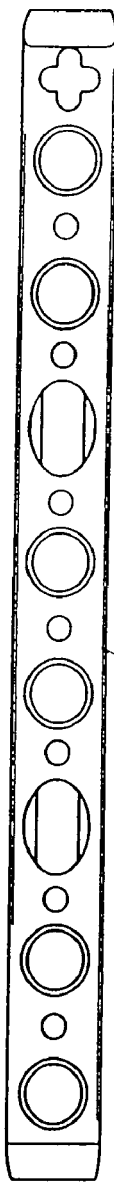
Figure 20:
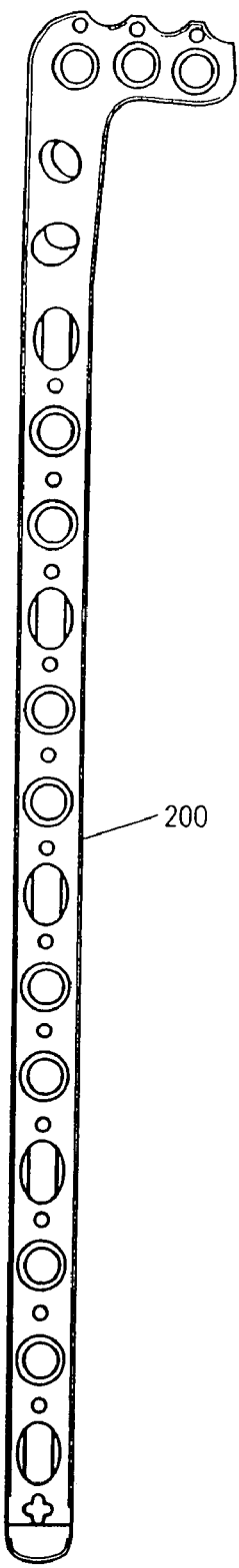
Figure 24:
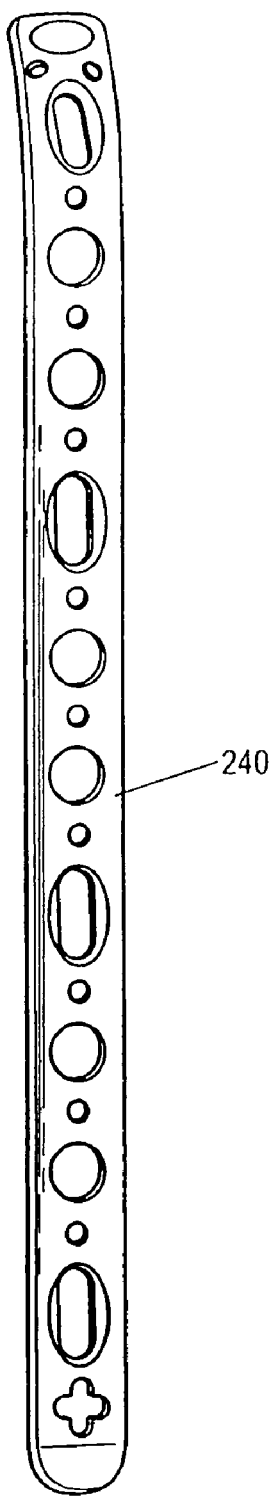
Figure 25:
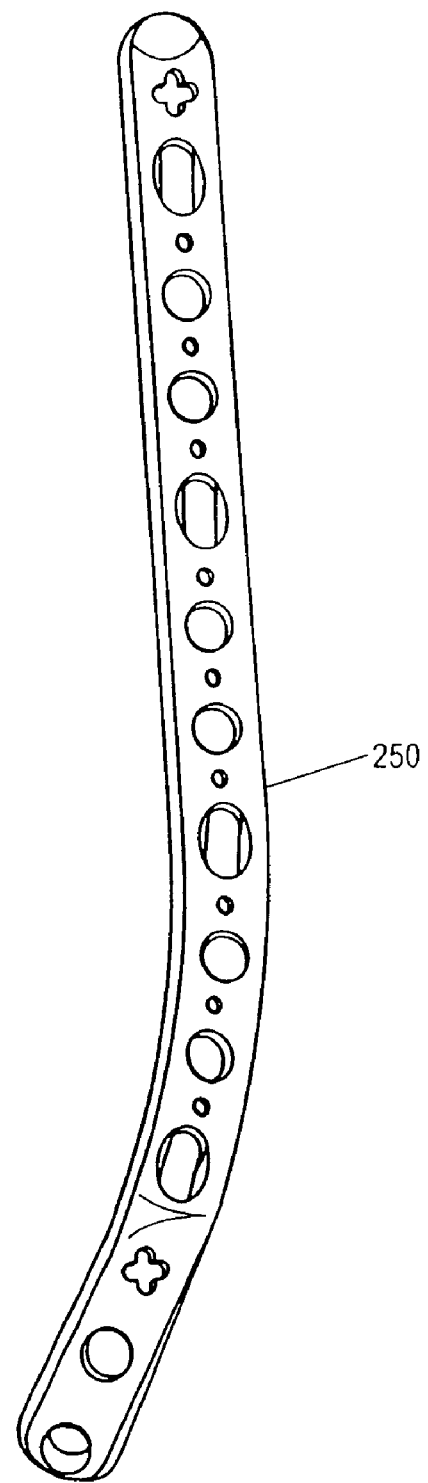
Figure 26:
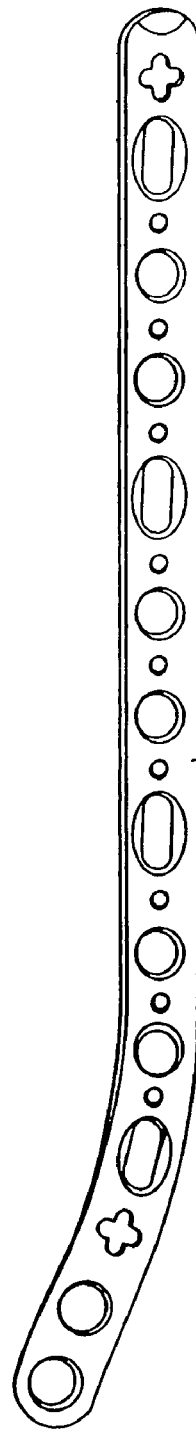
Figure 28:
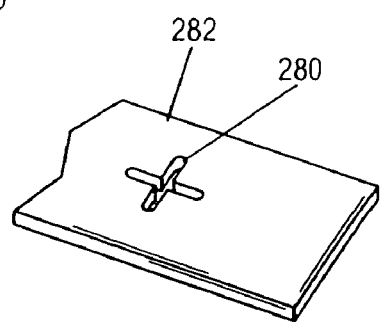
FIG. 28 shows a provisional fixation slot according to one embodiment of the present invention.

Shown in some of the exemplary bone plates in FIGS. 10-26 are provisional fixation slots, such as, for example, slots 280 in FIGS. 10 and 11, according to one embodiment of the present invention. FIG. 28 shows provisional fixation slot 280 in a portion of a bone plate 282. Methods of provisional fixation using such slots are further described in co-pending U.S. application Ser. No. 10/673,833. Additionally, more detailed information regarding provisional fixation of a bone plate to a bone prior to permanent attachment of the plate to the bone is provided in U.S. Pat. No. 5,676,667 to Hausman, issued Oct. 14, 1997, and U.S. Pat. No. 5,968,046 to Castleman, issued Oct. 19, 1999, each of which is incorporated herein by reference in its entirety.

Preferably, certain embodiments of bone plates according to this invention include an upper surface, a bone contacting surface, and a plurality of holes extending through the upper surface and the bone contacting surface. Each hole may interchangeably receive locking and compression screw and includes a thread that makes a complete revolution around the hole (exemplary embodiments of such holes are hole 52 and hole 92 described above), and no other non-threaded holes or openings for receiving bone screws are present in the plates. Certain embodiments may also include non-threaded pinholes that are not capable of receiving bone screws, but which may be used for provisional fixation with provisional fixation pins.

Figure 27:
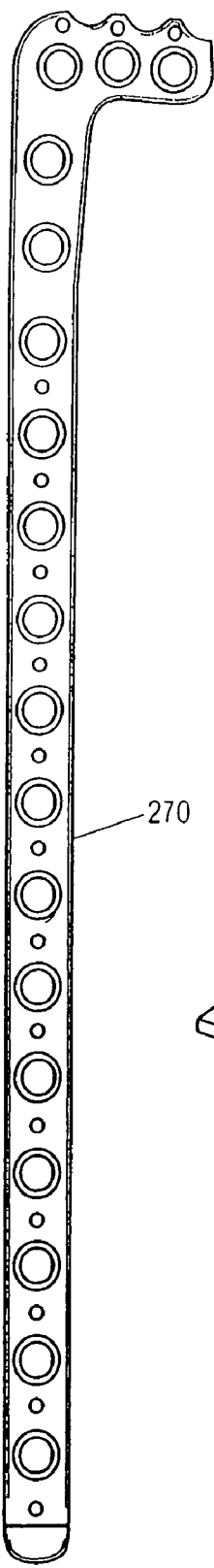
Figure 29:
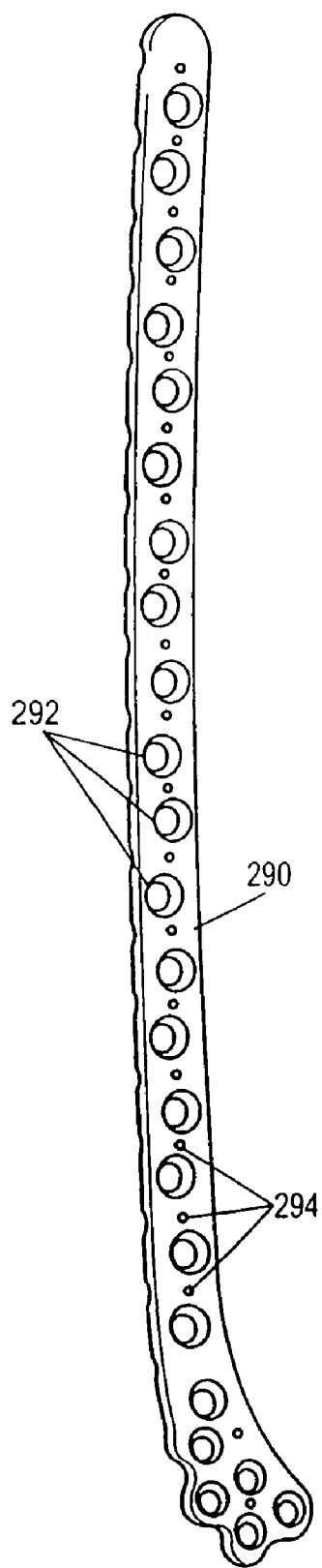
FIGS. 29-33 are perspective views of various exemplary bone plate configurations according to various embodiments of the present invention.
Figure 30:
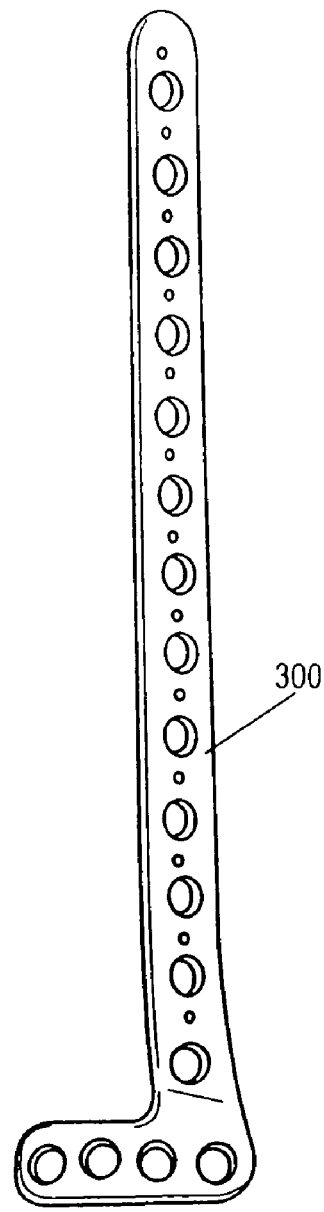

Several exemplary embodiments of such bone plates are shown in FIGS. 27 and 29-33. For example, FIG. 29 shows a distal femur plate 290 contoured to treat fractures of the distal femur from the lateral side of the bone. Each hole 292 may interchangeably receive locking and compression screw and includes a thread (not shown) that makes a complete revolution around the hole. Pinholes 294 are also included, but pinholes 294 are too small to receive bone screws, are not threaded, and are used for provisional fixation accomplished with provisional fixation pins. The plates shown in FIGS. 27 and 30-33 likewise have holes and pinholes like holes 292 and pinholes 294 described above. FIG. 27 shows a proximal tibia plate 270 contoured to treat proximal tibia fractures from the medial side. FIG. 30 shows an anterior lateral distal plate 300.

Figure 31:
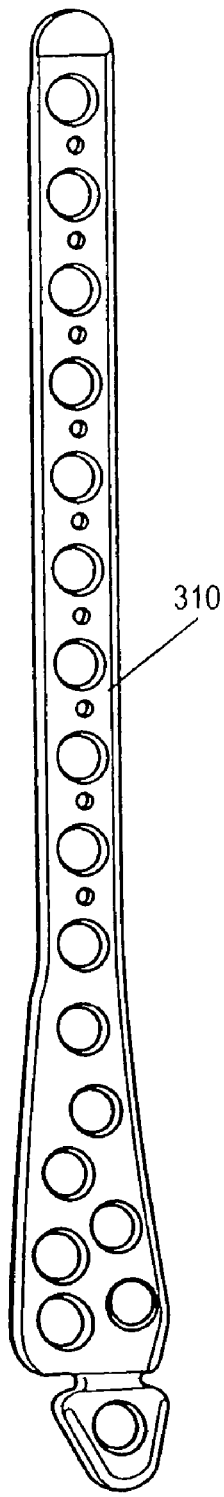
Figure 32:
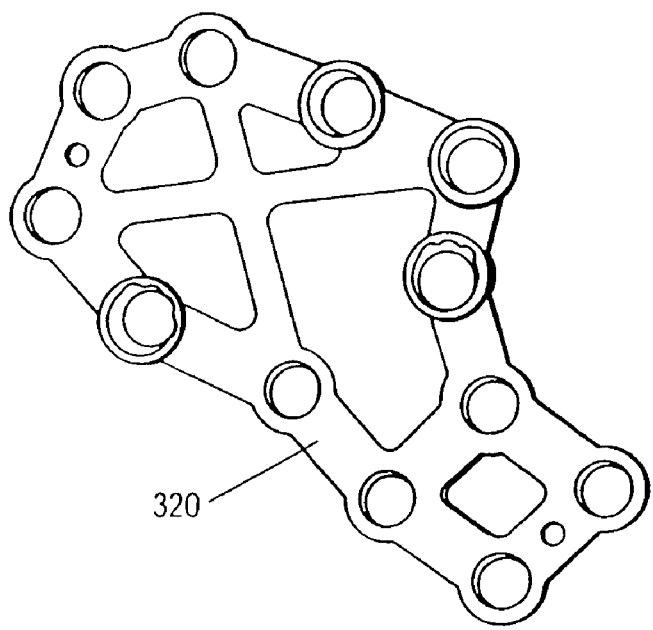
Figure 33:
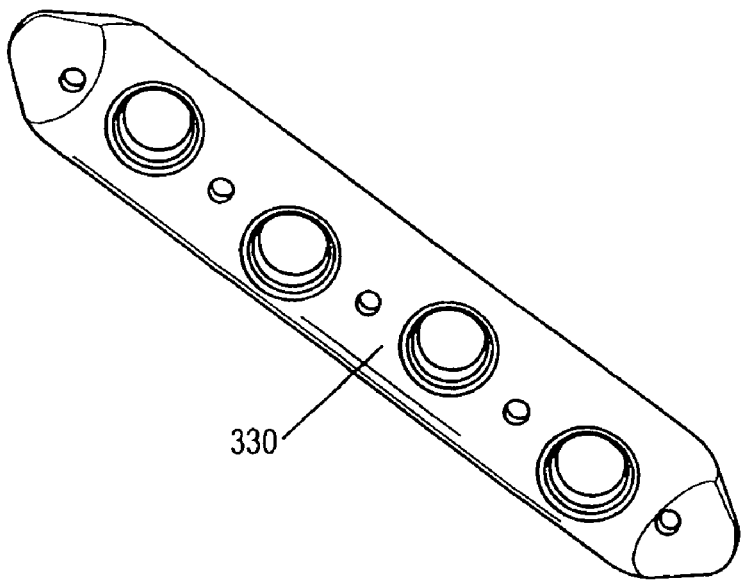

FIG. 31 shows a medial distal tibia plate 310. FIG. 32 shows a calcaneal plate 320 that is applied to the medial aspect of the calcaneus and used to treat calcaneal fractures. FIG. 33 shows a straight plate 330 used to treat small bone fractures. It should be understood that numerous other types or shapes of bone plates may be made such that every screw-receiving hole in the bone plate may interchangeably receive locking and compression screws and includes a thread that makes a complete revolution around the hole.

An exemplary embodiment of a method of fracture reduction utilizing provisional fixation pins through a screw-receiving hole of a bone plate is described below. Numerous other exemplary embodiments of methods of fracture reduction using compression screws and/or locking screws, as well as, optionally, provisional fixation pins, are further described in co-pending U.S. application Ser. No. 10/673,833, which is incorporated herein by reference.

A fracture is reduced with conventional forceps, and a bone plate of appropriate size and shape is placed over the fracture site. The bone plate is temporarily secured to the bone using provisional fixation pins. In a bone plate such as those shown in FIGS. 27 and 29-33 described above, provisional fixation pins may be used through either the pinholes or the screw-receiving holes of the bone plate. For example, a 2 mm diameter provisional fixation pin may be used through a pinhole, a 2.7 mm diameter provisional fixation pin may be used through a 3.5 mm screw-receiving hole, and a 3.5 mm diameter provisional fixation pin may be used through a 4.5 mm screw-receiving hole. In one embodiment, provisional fixation is accomplished through the screw-receiving holes only.

Once one or more provisional fixation pins are used through these holes to secure the bone plate to the bone temporarily, a hole is drilled in the bone through one of the other screw-receiving holes of the bone plate. A locking or compression screw with an appropriate head diameter is then inserted into the bone for fixation or for lagging bone fragments to the plate. Provisional fixation provides for temporarily securing the bone plate to the bone before placing fixation screws through the bone plate, so that one can be certain the bone plate is properly positioned before placing bone screws for permanent fixation of the bone plate to the bone. Moreover, with provisional fixation, x-rays can be taken of the bone plate/construct without excess instruments in the field of view.

The foregoing description of exemplary embodiments of the invention has been presented only for the purposes of illustration and description and is not intended to be exhaustive or to limit the invention to the precise forms disclosed. Many modifications and variations are possible in light of the above disclosure. The embodiments were chosen and described in order to explain the principles of the invention and their practical application so as to enable others skilled in the art to make and utilize the invention and various embodiments and with various modifications as are suited to the particular use contemplated. Alternative embodiments will become apparent to those skilled in the art to which the present invention pertains without departing from its spirit and scope.

What is claimed is:

1. A bone plate system for reducing a fracture of a bone, the system comprising:
    a bone plate comprising an upper surface, a lower surface, and a hole extending between the upper and lower surfaces;
    the hole comprising a frustoconical portion, an upper opening at the upper surface, and a lower opening at the lower surface, the lower opening having a first diameter, the upper opening having a second diameter that is greater than the first diameter, and the frustoconical portion having a smooth tapered first portion extending from the upper surface and a preformed, threaded tapered second portion extending from the lower surface, the first and second portions being tapered at different angles and a smallest diameter of the hole is the first diameter;
    a fastener comprising a head and a bone engagement portion, the head comprising a spherical portion and the bone engagement portion having a third diameter less than the first diameter, wherein the spherical portion of the head engages the frustoconical portion of the hole when the fastener is inserted into the hole and the bone engagement portion engages the bone; and
    an opening for receiving a provisional fixation pin, the opening having a diameter less than the first diameter.

2. The system of claim 1, further comprising a second fastener with a threaded head and a bone engagement portion, wherein the threaded head is configured to threadably engage the hole.

3. The system of claim 1, wherein the opening for receiving a provisional fixation pin includes a cross-shaped slot.

4. The system of claim 1, wherein the hole includes a thread that makes at least one complete revolution around the hole.

5. The system of claim 1, wherein the upper opening extends downward from the upper surface at a first angle relative to a longitudinal axis extending through a center of the hole, and the lower opening extends downward toward the lower surface at a second angle relative to the longitudinal axis of the hole, wherein the second angle is substantially less than the first angle.

6. A bone plate for reducing a fracture of a bone, the bone plate comprising:
    an upper surface;
    a lower surface; and
    a hole extending between the upper and lower surfaces, the hole comprising an upper opening at the upper surface, a lower opening at the lower surface, a first frustoconical portion having a smooth tapered first portion extending from the upper surface, and a preformed, threaded tapered second portion extending from the lower surface, the lower opening having a first diameter and the upper opening having a second diameter that is greater than the first diameter, the first and second portions being tapered at different angles and a smallest diameter of the hole is the first diameter.

7. The bone plate of claim 6, wherein the bone plate further comprises a plurality of provisional fixation openings, each opening having a diameter less than the first diameter.

8. The bone plate of claim 7, wherein at least one of the plurality of openings is a cross-shaped slot.

9. The bone plate of claim 6, wherein the hole includes a thread that makes at least one complete revolution around the hole.

10. The bone plate of claim 6, wherein the upper opening extends downward from the upper surface at a first angle relative to a longitudinal axis extending through a center of the hole, and the lower opening extends downward toward the lower surface at a second angle relative to the longitudinal axis of the hole, wherein the second angle is substantially less than the first angle.

* * * * *